(12) United States Patent
Pease et al.

(10) Patent No.: US 7,374,571 B2
(45) Date of Patent: *May 20, 2008

(54) ROLLED MINIMALLY-INVASIVE HEART VALVES AND METHODS OF MANUFACTURE

(75) Inventors: Matthew L. Pease, Mountain View, CA (US); Brandon G. Walsh, Livermore, CA (US); Jibin Yang, Aliso Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1195 days.

This patent is subject to a terminal disclaimer.

(21) Appl. No.: 10/286,009

(22) Filed: Nov. 1, 2002
(Under 37 CFR 1.47)

(65) Prior Publication Data

US 2003/0055495 A1    Mar. 20, 2003

Related U.S. Application Data

(63) Continuation-in-part of application No. 09/815,521, filed on Mar. 23, 2001, now Pat. No. 6,733,525, and a continuation-in-part of application No. 09/951,701, filed on Sep. 13, 2001.

(51) Int. Cl.
*A61F 2/24*    (2006.01)
(52) U.S. Cl. .................................................. 623/2.12
(58) Field of Classification Search ............... 623/1.12, 623/1.17, 1.22, 1.24, 1.26, 2.12–2.19
See application file for complete search history.

(56) References Cited

U.S. PATENT DOCUMENTS 3,409,013 A    11/1968   Berry

| 3,671,979 A | 6/1972 | Moulopoulos |
| 4,056,854 A | 11/1977 | Boretos et al. |
| 4,106,129 A | 8/1978 | Carpentier et al. |

(Continued)

FOREIGN PATENT DOCUMENTS

DE    036 40 745 A1    6/1987

(Continued)

*Primary Examiner*—Corrine McDermott
*Assistant Examiner*—Cheryl Miller
(74) *Attorney, Agent, or Firm*—Guy Cumberbatch; David L. Hauser

(57) ABSTRACT

Expandable heart valves for minimally invasive valve replacement surgeries are disclosed. The valves are rolled into a first, contracted configuration for minimally invasive delivery using a catheter, and then unrolled or unfurled at the implantation site. One- and two-piece stents may be used in conjunction with a plurality of flexible leaflet-forming membranes. The stents may include an annulus section, a sinus section with the membranes attached over sinus apertures, and an outflow section. Lockout tabs and making slots secure the stents in their expanded shapes. Alignment structure ensures concentric unfurling of the stent. Anchoring elements at the stent edges or in the stent body secure the valve within the annulus. A method of manufacture includes shape setting the sheet-like stent to ensure an outward bias during deployment. The stent may also include dear tracks for engagement with a gear mechanism for deployment. The stent is desirably made of a superelastic material such as Nitinol and may have areas removed or thinned to reduce the bending stresses when rolled into its small spiral for catheter delivery.

33 Claims, 18 Drawing Sheets

U.S. PATENT DOCUMENTS

| | | | |
|---|---|---|---|
| 4,297,749 A | 11/1981 | Davis et al. | |
| 4,364,126 A * | 12/1982 | Rosen et al. | 623/2.38 |
| 4,680,031 A * | 7/1987 | Alonso | 623/2.13 |
| 4,878,906 A | 11/1989 | Lindemann et al. | |
| 4,922,905 A | 5/1990 | Strecker | |
| 4,960,424 A | 10/1990 | Grooters | |
| 4,994,077 A | 2/1991 | Dobben | |
| 5,078,726 A | 1/1992 | Kreamer | |
| 5,123,917 A | 6/1992 | Lee | |
| 5,147,370 A | 9/1992 | McNamara et al. | |
| 5,163,953 A | 11/1992 | Vince | |
| 5,266,073 A | 11/1993 | Wall | |
| 5,306,294 A | 4/1994 | Winston et al. | |
| 5,332,402 A | 7/1994 | Teitelbaum | |
| 5,344,426 A | 9/1994 | Lau et al. | |
| 5,366,473 A | 11/1994 | Winston et al. | |
| 5,370,685 A | 12/1994 | Stevens | |
| 5,397,351 A | 3/1995 | Pavcnik et al. | |
| 5,411,552 A | 5/1995 | Andersen et al. | |
| 5,443,500 A * | 8/1995 | Sigwart | 623/1.17 |
| 5,545,214 A | 8/1996 | Stevens | |
| 5,545,215 A | 8/1996 | Duran | |
| 5,554,185 A | 9/1996 | Block et al. | |
| 5,556,413 A | 9/1996 | Lam | |
| 5,593,434 A | 1/1997 | Williams | |
| 5,607,465 A | 3/1997 | Camilli | |
| 5,618,299 A | 4/1997 | Khosravi et al. | |
| 5,634,941 A | 6/1997 | Winston et al. | |
| 5,682,906 A | 11/1997 | Sterman et al. | |
| 5,713,951 A | 2/1998 | Garrison et al. | |
| 5,716,370 A | 2/1998 | Williamson, IV et al. | |
| 5,723,003 A | 3/1998 | Winston et al. | |
| 5,728,151 A | 3/1998 | Garrison et al. | |
| 5,752,526 A | 5/1998 | Cosgrove | |
| 5,769,812 A | 6/1998 | Stevens et al. | |
| 5,810,847 A | 9/1998 | Laufer et al. | |
| 5,810,870 A | 9/1998 | Myers et al. | |
| 5,824,046 A | 10/1998 | Smith et al. | |
| 5,824,064 A | 10/1998 | Taheri | |
| 5,840,081 A | 11/1998 | Andersen et al. | |
| RE35,988 E | 12/1998 | Winston et al. | |
| 5,855,597 A | 1/1999 | Jayaraman | |
| 5,855,601 A | 1/1999 | Bessler et al. | |
| 5,873,907 A | 2/1999 | Frantzen | |
| 5,876,419 A * | 3/1999 | Carpenter et al. | 623/1.16 |
| 5,910,170 A | 6/1999 | Reimink et al. | |
| 5,925,063 A * | 7/1999 | Khosravi | 606/200 |
| 5,957,949 A | 9/1999 | Leonhardt et al. | |
| 5,984,963 A | 11/1999 | Ryan et al. | |
| 5,993,489 A | 11/1999 | Lewis et al. | |
| 6,010,531 A | 1/2000 | Donlon et al. | |
| 6,015,430 A | 1/2000 | Wall | |
| 6,027,525 A | 2/2000 | Suh et al. | |
| 6,042,607 A | 3/2000 | Williamson, IV et al. | |
| 6,048,360 A | 4/2000 | Khosravi et al. | |
| 6,074,418 A | 6/2000 | Buchanan et al. | |
| 6,083,219 A | 7/2000 | Laufer | |
| 6,092,529 A | 7/2000 | Cox | |
| 6,096,074 A | 8/2000 | Pedros | |
| 6,099,498 A | 8/2000 | Addis | |
| 6,102,943 A | 8/2000 | McGuinness | |
| 6,106,550 A | 8/2000 | Magovern et al. | |
| 6,162,208 A | 12/2000 | Hipps | |
| 6,162,233 A | 12/2000 | Williamson, IV et al. | |
| 6,168,614 B1 | 1/2001 | Andersen et al. | |
| 6,176,877 B1 | 1/2001 | Buchanan et al. | |
| 6,203,553 B1 | 3/2001 | Robertson et al. | |
| 6,221,091 B1 | 4/2001 | Khosravi | |
| 6,264,691 B1 | 7/2001 | Gabbay | |
| 6,269,819 B1 | 8/2001 | Oz et al. | |
| 6,283,127 B1 | 9/2001 | Sterman et al. | |
| 6,287,334 B1 * | 9/2001 | Moll et al. | 623/1.24 |
| 6,287,339 B1 | 9/2001 | Vazquez et al. | |
| 6,309,382 B1 | 10/2001 | Garrison et al. | |
| 6,309,417 B1 * | 10/2001 | Spence et al. | 623/2.11 |
| 6,319,281 B1 | 11/2001 | Patel | |
| 6,425,916 B1 | 7/2002 | Garrison et al. | |
| 6,454,799 B1 | 9/2002 | Schreck | |
| 6,733,525 B2 * | 5/2004 | Yang et al. | 623/2.18 |
| 7,156,872 B2 * | 1/2007 | Strecker | 623/1.24 |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0021872 A1 | 9/2001 | Bailey et al. | |
| 2001/0031972 A1 | 10/2001 | Robertson et al. | |
| 2001/0044591 A1 | 11/2001 | Stevens et al. | |
| 2001/0044656 A1 | 11/2001 | Williamson, IV et al. | |

FOREIGN PATENT DOCUMENTS

| | | |
|---|---|---|
| DE | 198 57 887 A1 | 7/2000 |
| EP | 0 382 014 A1 | 8/1990 |
| EP | 0 145 166 B2 | 6/1995 |
| EP | 0 592 410 B1 | 10/1995 |
| EP | 0 737 453 A2 | 10/1996 |
| EP | 0 756 853 A1 | 2/1997 |
| EP | 1 034 753 | 9/2000 |
| EP | 1 057 460 A1 | 12/2000 |
| EP | 1 088 529 A2 | 4/2001 |
| GB | 2 056 023 A | 3/1981 |
| SU | 127508 A1 | 11/1986 |
| WO | WO 91/17720 A1 | 11/1991 |
| WO | WO 96/02212 A1 | 2/1996 |
| WO | WO 95/19159 A1 | 6/1996 |
| WO | WO 97/12563 A1 | 4/1997 |
| WO | WO 97/12565 A1 | 4/1997 |
| WO | WO 97/27799 A1 | 8/1997 |
| WO | WO 97/30659 A1 | 8/1997 |
| WO | WO 98/11846 A1 | 3/1998 |
| WO | WO 98/29057 A1 | 7/1998 |
| WO | WO 98/57599 A2 | 12/1998 |
| WO | WO 99/15112 A1 | 4/1999 |
| WO | WO 99/33414 A1 | 7/1999 |
| WO | WO 00/00107 A1 | 1/2000 |
| WO | WO 00/41632 A1 | 7/2000 |
| WO | WO 00/41652 A1 | 7/2000 |
| WO | WO 00/44313 A1 | 8/2000 |
| WO | WO 00/45874 A1 | 8/2000 |
| WO | WO 00/47139 A1 | 8/2000 |
| WO | WO 00/48533 A1 | 8/2000 |
| WO | WO 00/61034 A1 | 10/2000 |
| WO | WO 01/19285 A1 | 3/2001 |
| WO | WO 01/26586 A1 | 4/2001 |
| WO | WO 01/52775 A1 | 7/2001 |
| WO | WO 01/54625 A1 | 8/2001 |
| WO | WO 01/56512 A1 | 8/2001 |
| WO | WO 01/62189 A1 | 8/2001 |
| WO | WO 01/64137 A1 | 9/2001 |

* cited by examiner

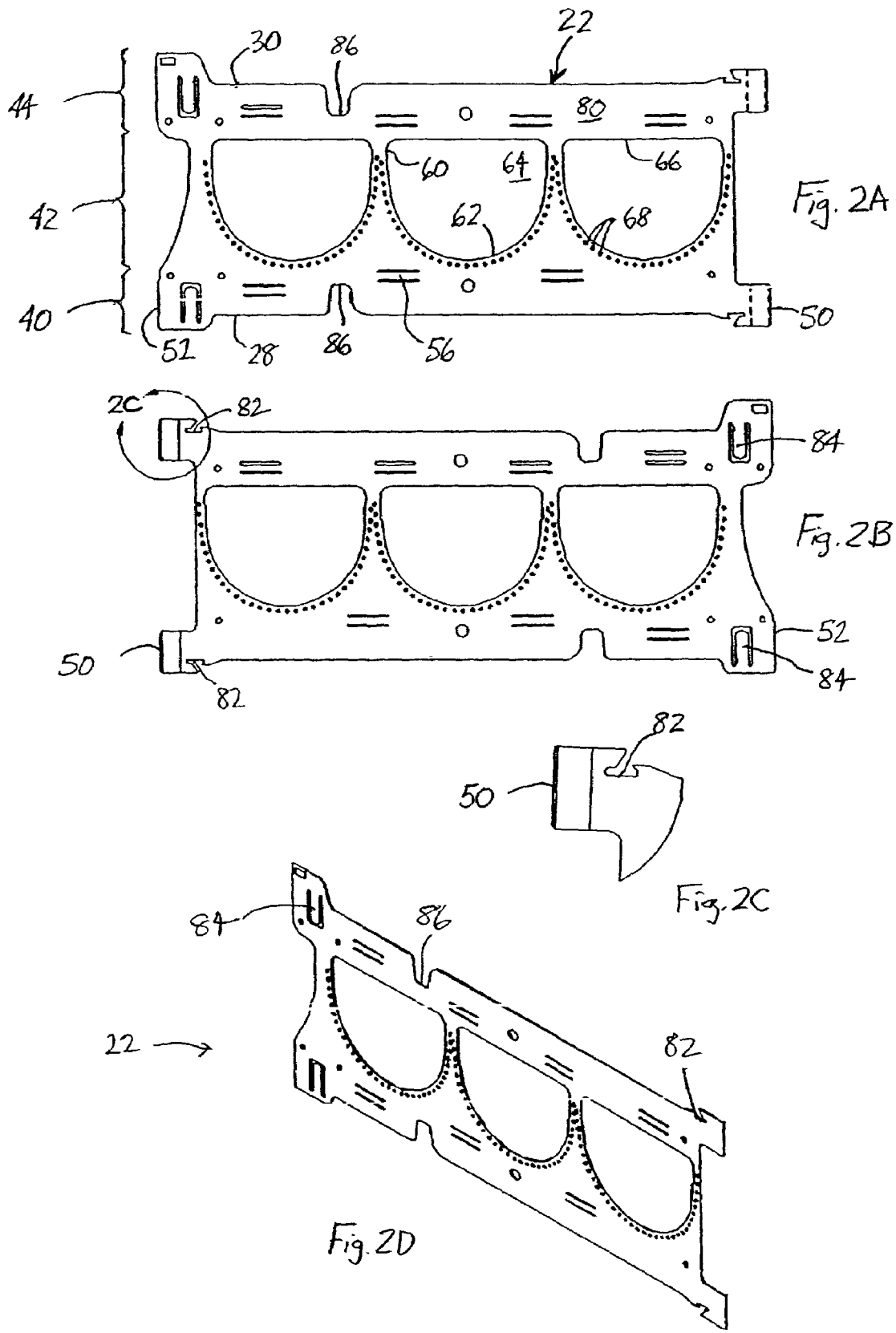

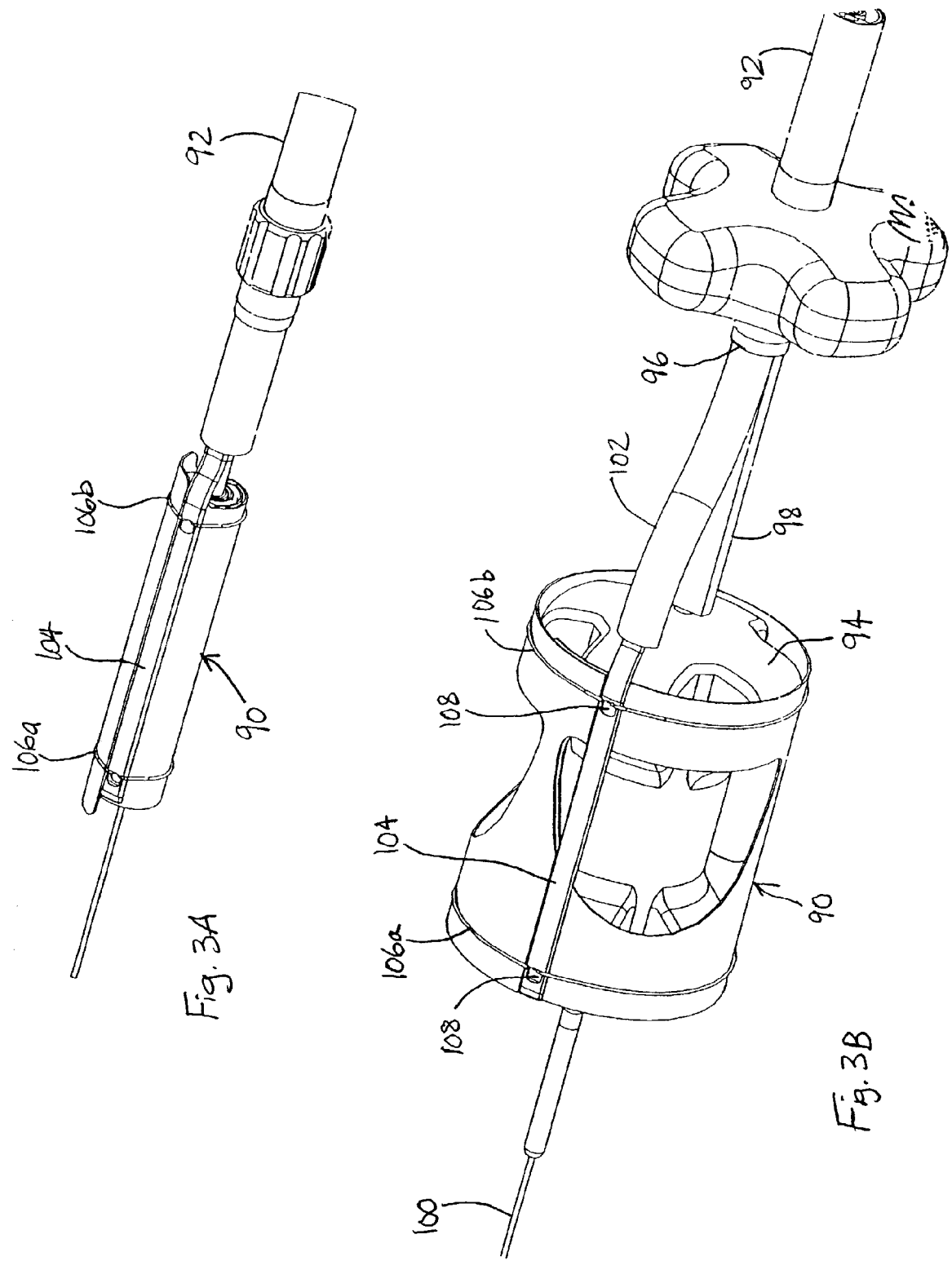

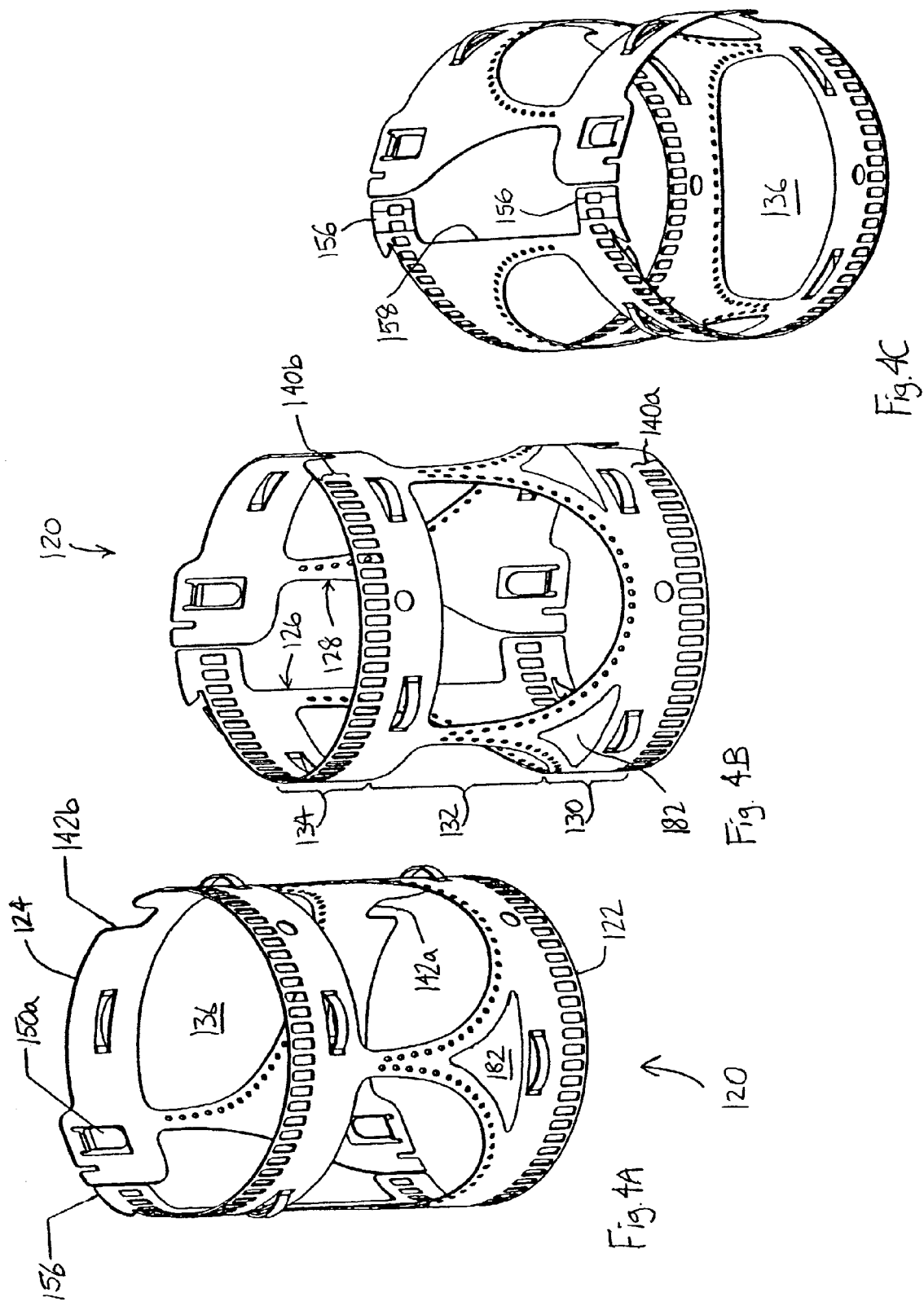

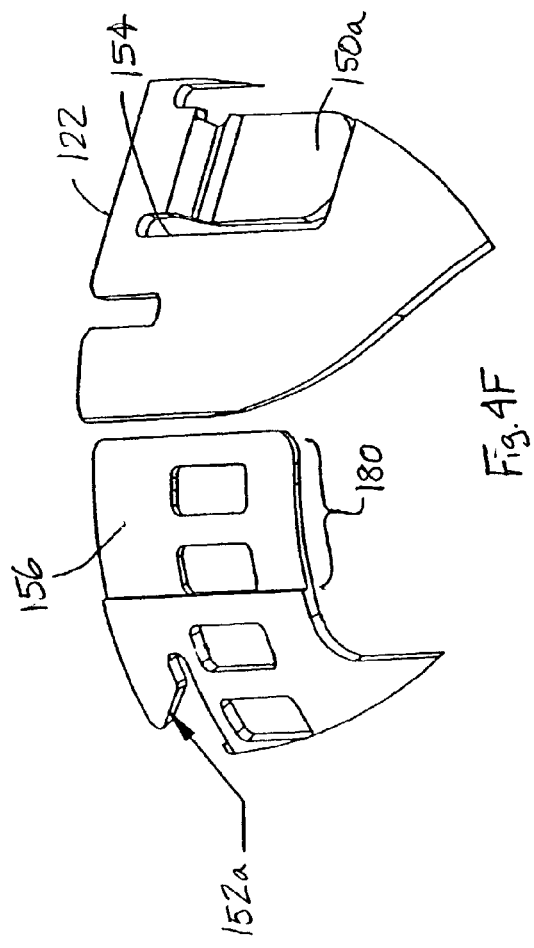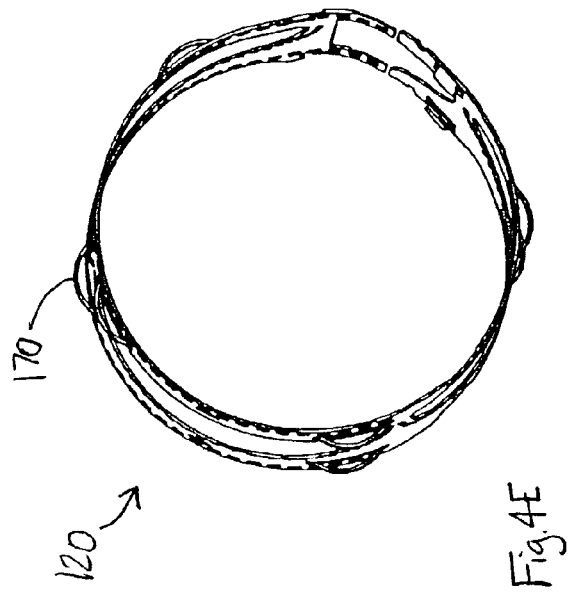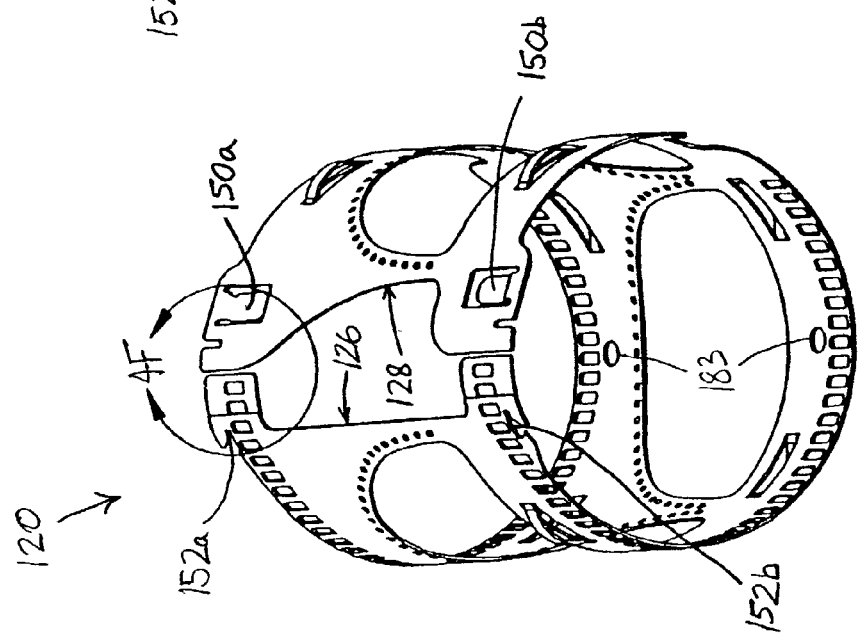

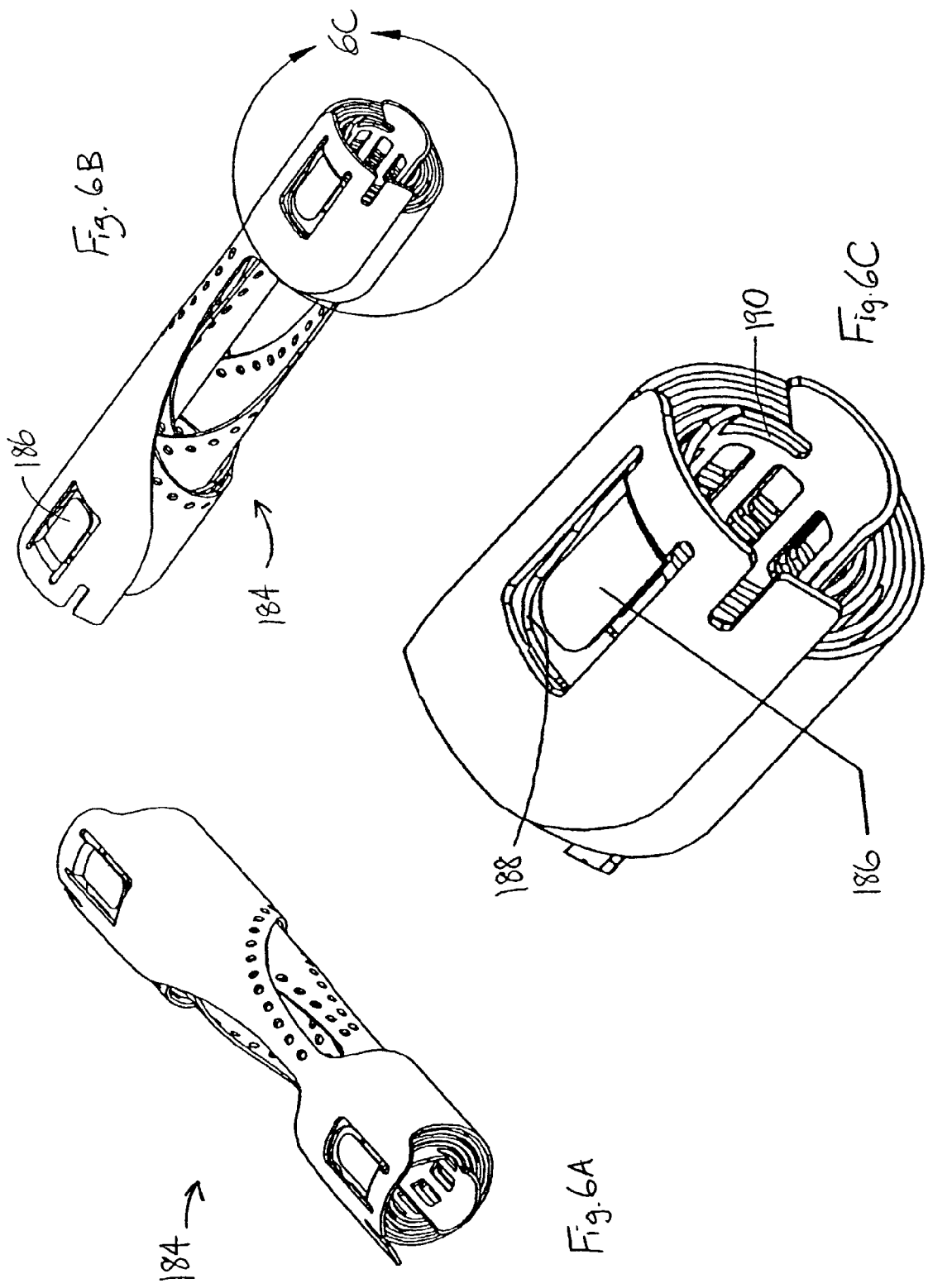

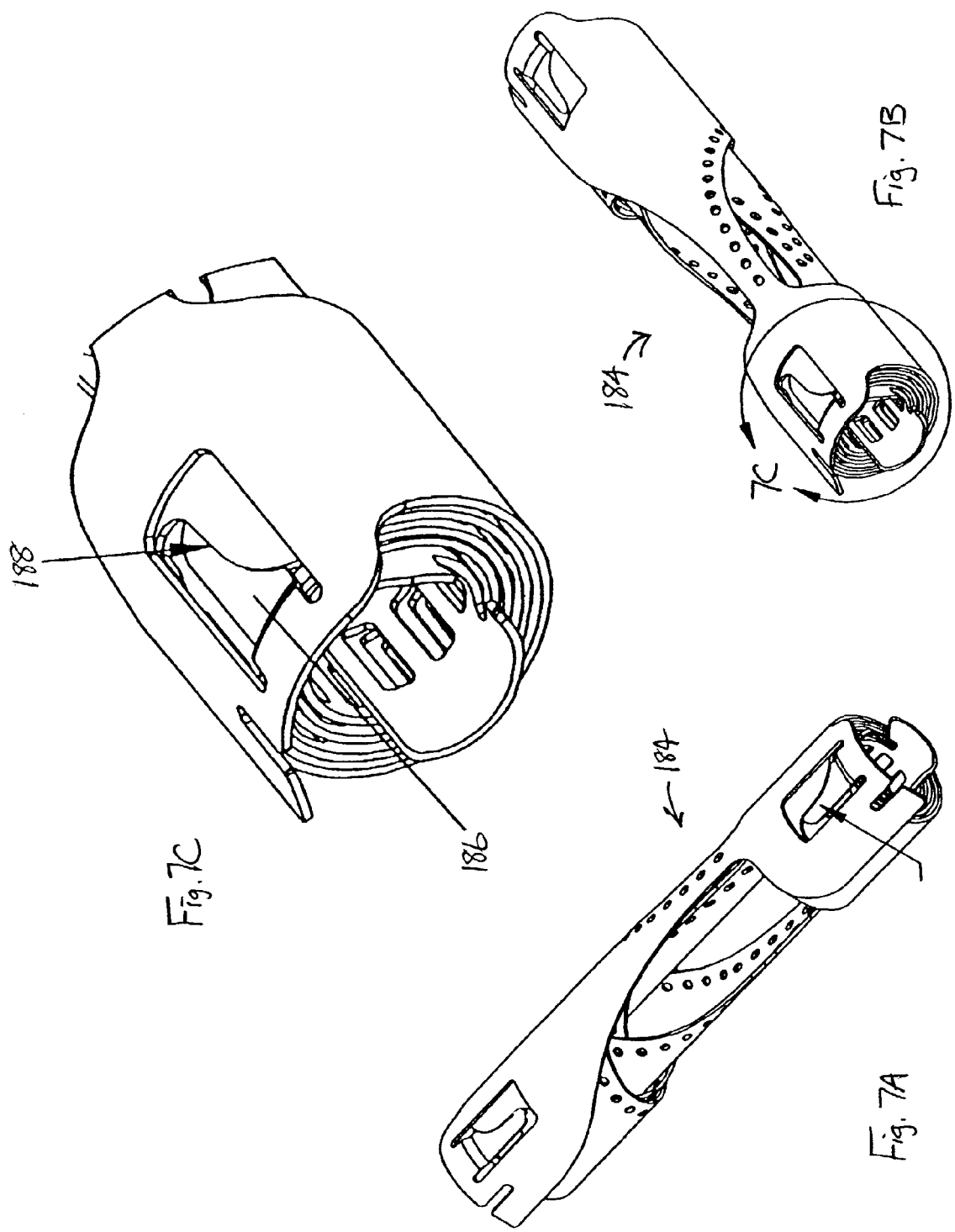

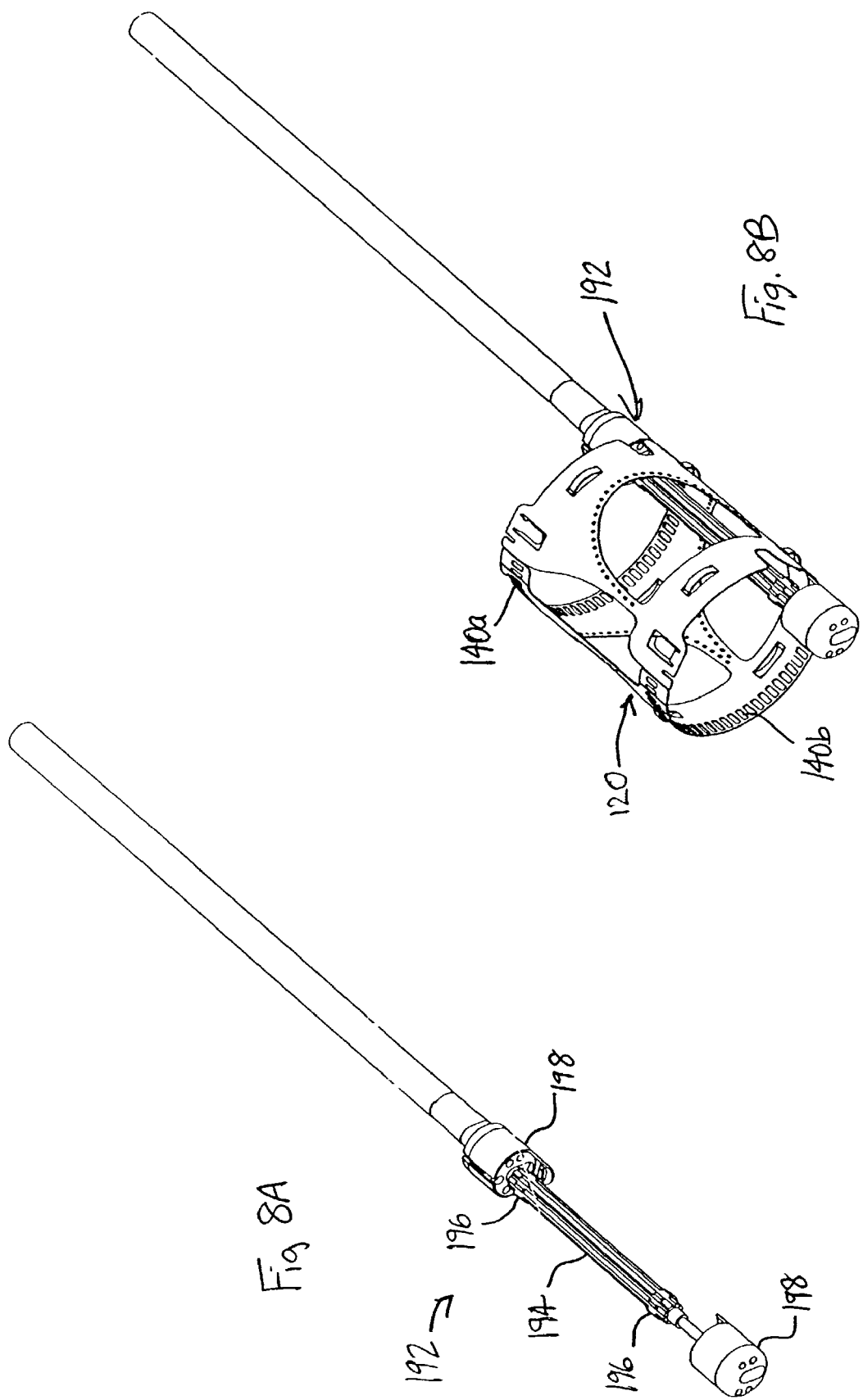

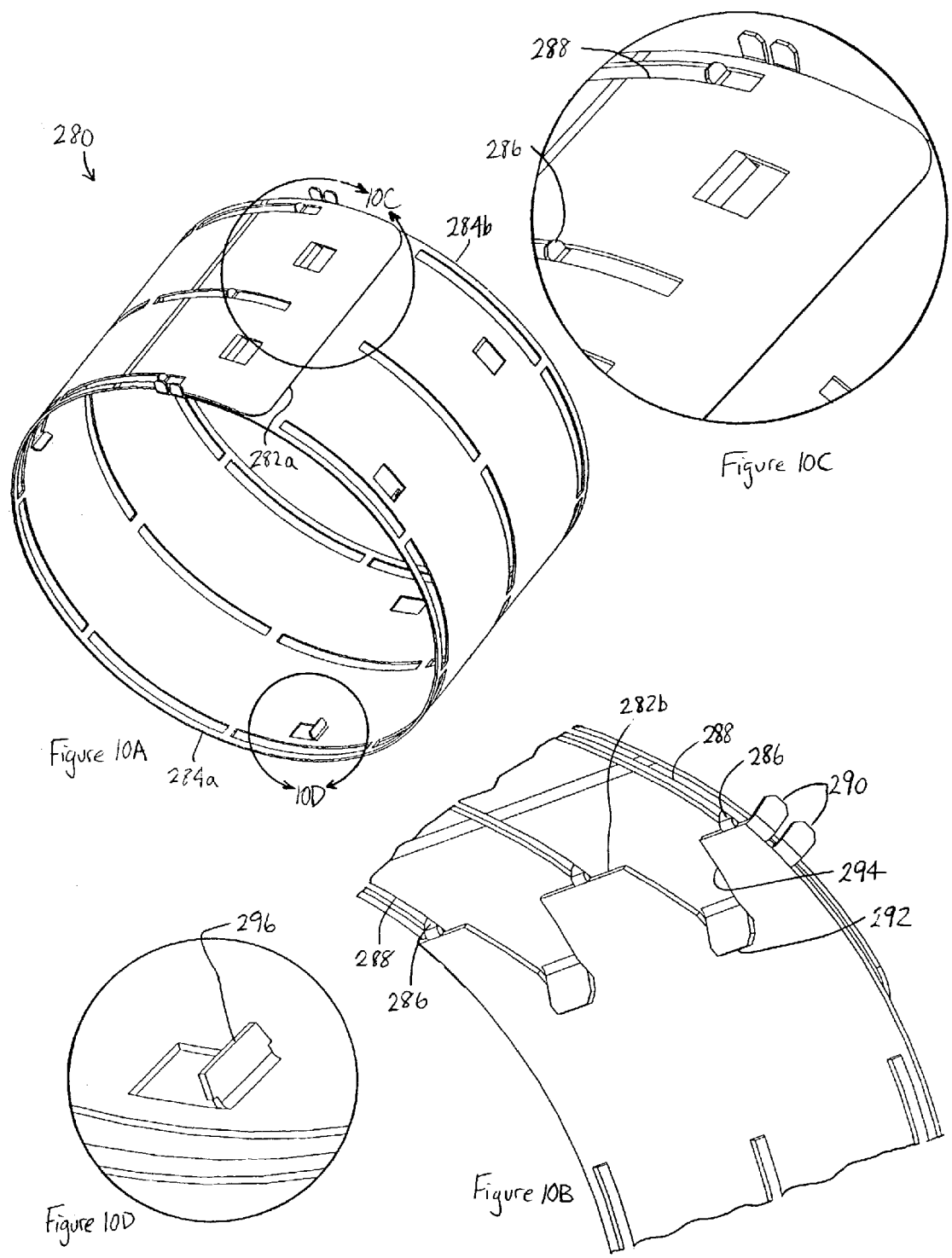

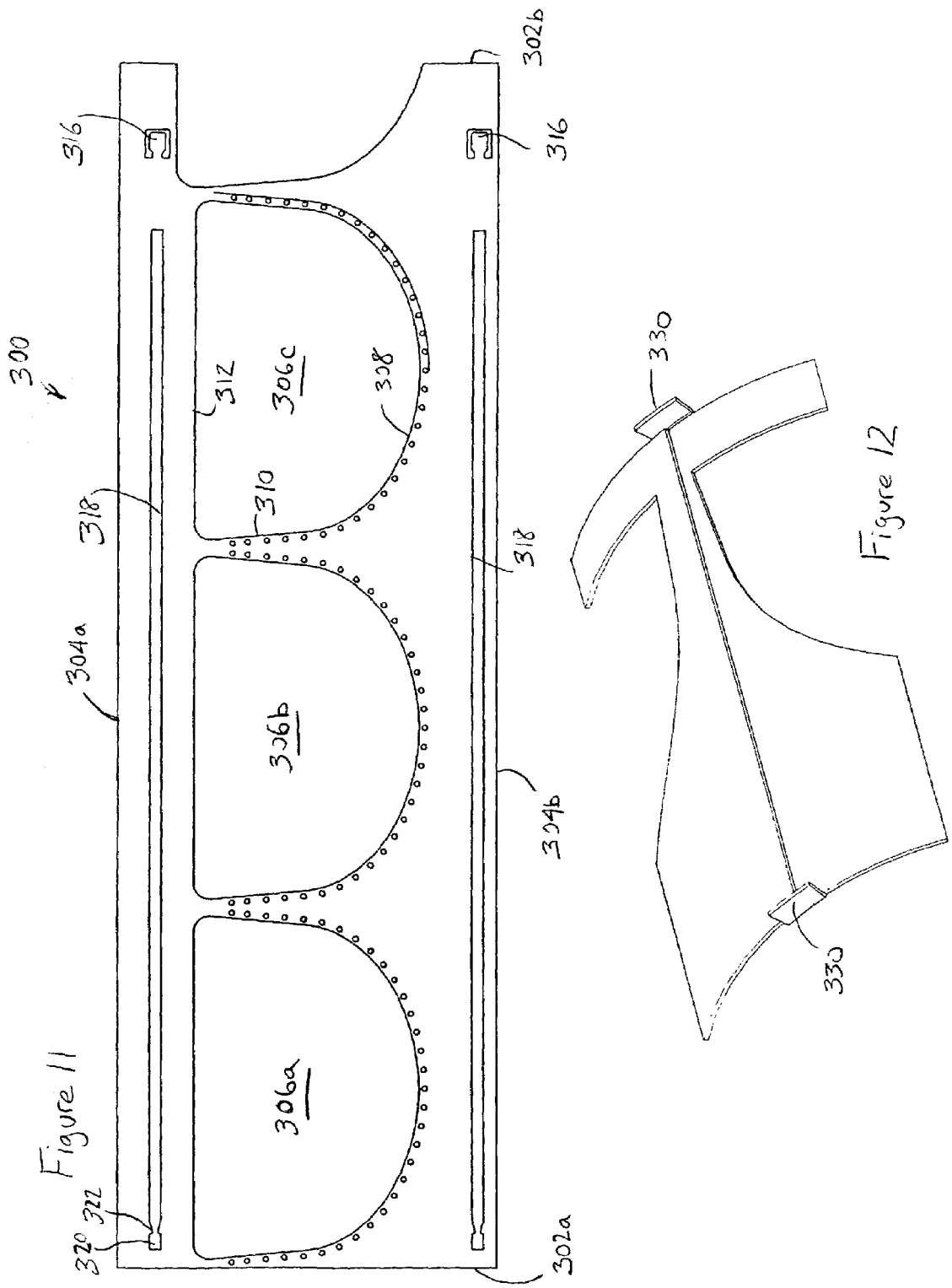

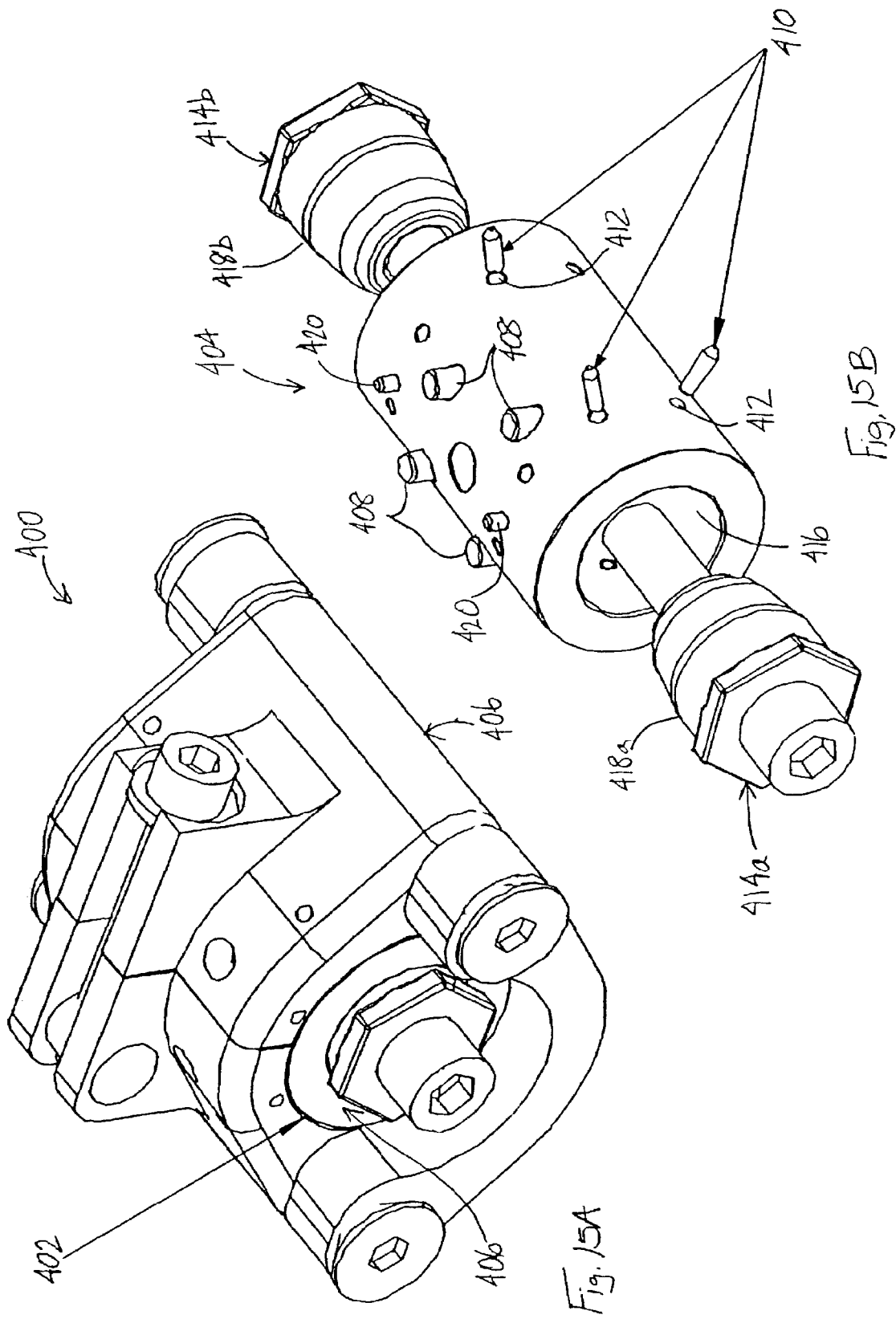

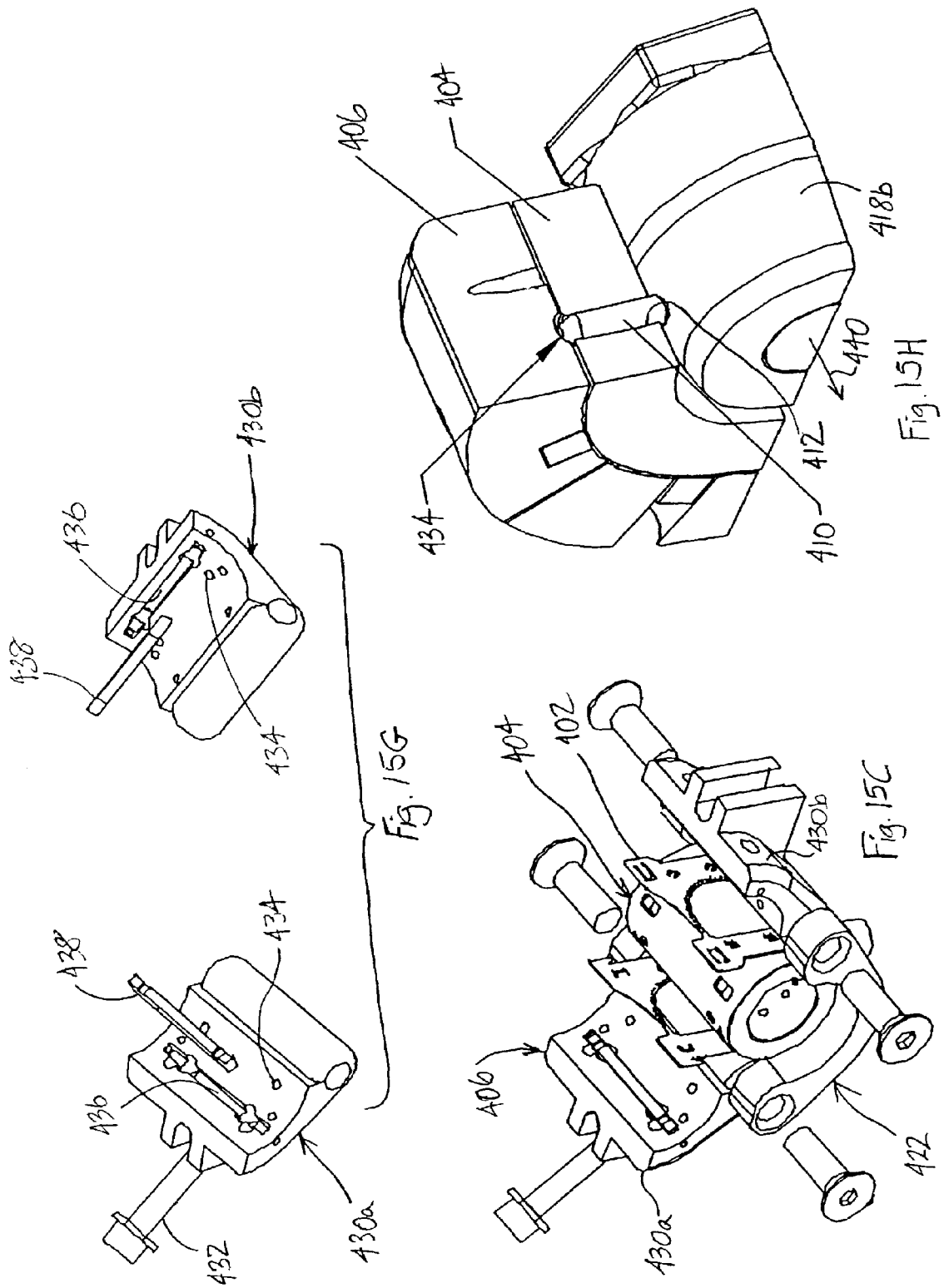

ROLLED MINIMALLY-INVASIVE HEART VALVES AND METHODS OF MANUFACTURE

RELATED APPLICATIONS

The present application is a continuation-in-part of U.S. application Ser. No. 09/815,521, entitled "ROLLED MINIMALLY-INVASIVE HEART VALVES AND METHODS OF USE," filed Mar. 23, 2001, now U.S. Pat. No. 6,733,525, and is a continuation-in-part of U.S. application Ser. No. 09/951,701, entitled "METHODS AND APPARATUSES FOR DEPLOYING MINIMALLY-INVASIVE HEART VALVES," filed Sep. 13, 2001.

FIELD OF THE INVENTION

The present invention relates generally to medical devices and particularly to expandable heart valve prostheses especially for use in minimally-invasive surgeries.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves, although repair or replacement of the aortic or mitral valves is most common because they reside in the left side of the heart where pressures are the greatest.

Where replacement of a heart valve is indicated, the dysfunctional valve is typically cut out and replaced with either a mechanical valve, or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment. Importantly, the wireform provides continuous support for each leaflet along the cusp region so as to better simulate the natural support structure.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Some attempts have been made to enable less traumatic delivery and implantation of prosthetic heart valves. For instance, U.S. Pat. No. 4,056,854 to Boretos discloses a radially collapsible heart valve secured to a circular spring stent that can be compressed for delivery and expanded for securing in a valve position. Also, U.S. Pat. No. 4,994,077 to Dobbin describes a disk-shaped heart valve that is connected to a radially collapsible stent for minimally invasive implantation.

Recently, a great amount of research has been done to reduce the trauma and risk associated with conventional open heart valve replacement surgery. In particular, the field of minimally invasive surgery (MIS) has exploded since the early to mid-1990s, with devices now being available to enable valve replacements without opening the chest cavity. MIS heart valve replacement surgery still typically requires bypass, but the excision of the native valve and implantation of the prosthetic valve are accomplished via elongated tubes or cannulas, with the help of endoscopes and other such visualization techniques.

Some examples of more recent MIS heart valves are shown in U.S. Pat. No. 5,411,552 to Anderson, et al., U.S. Pat. No. 5,980,570 to Simpson, U.S. Pat. No. 5,984,959 to Robertson, et al., PCT Publication No. 00/047139 to Garrison, et al., and PCT Publication No. WO 99/334142 to Vesely. Although these and other such devices provide various ways for collapsing, delivering, and then expanding a "heart valve" per se, none of them disclose an optimum structure. For instance, the publication to Vesely shows a tissue leaflet structure of the prior art in FIG. 1, and an expandable inner frame of the invention having stent posts in FIGS. 3A-3C. The leaflets are "mounted to the stent posts 22 in a manner similar to that shown in FIG. 1." Such general disclosures as in Vesely stop short of explaining how to construct a valve in a manner that maximizes long-term efficacy. In particular, the means of attaching the leaflets to the MIS stent is critical to ensure the integrity and durability of the valve once implanted. All of the prior art MIS valves are inadequate in this regard.

Another problem with MIS valves of the prior art is their relatively large radial dimension during implantation. That is, these valves all utilize one or more radially-expanding stents, and the assembly must be compressed radially and then passed through the lumen of a large bore catheter. Reducing the radial profile of the constricted valve via radial compression is problematic and conflicts with the need for sufficient circumferential length of the valve in its expanded state to fit within an adult heart valve annulus. Moreover, radial compression of the stent in combination with a biological valve must be done with great care so as not to damage the valve.

Tubular stents in general are known, typically constructed of a tubular metal lattice that has a normal, relaxed diameter and is compressed for insertion into a vein or artery. Upon expulsion from the end of a catheter, the tubular metal lattice expands to its original larger diameter in contact with the vessel wall. It is important to note that there is no regulation of the self-expansion of the stent. Furthermore, stents of the prior art expand outward to the size of the expansion balloon, or until meeting resistance from the surrounding vessel, and so their final size varies. Minimally-invasive heart valves that use conventional tubular stents that are self- or plastically expanded outward by a balloon do not have a positive maximum size limit; that is, there is no structure preventing further expansion of the stent. The final diameter of the valve is determined by the maximum size of the balloon, which may over-expand into the surrounding annulus leading to a less than optimum fit. Alternatively, the surrounding annulus may provide sufficient resistance to further outward expansion of the balloon so as to stop expansion of the heart valve prior to its optimum size. That is, the valve may exhibit a loose fit in the annulus, potentially leading to migration.

Some MIS valves of the prior art are intended to be used without removing the natural valve leaflets. Sometimes the natural leaflets are heavily calcified, and their removal entails some risk of plaque particles being released into the bloodstream. Therefore, some of the MIS valves are designed to expand outward within the annulus and native leaflets, and compress the leaflets against the annulus. In doing so, a relatively uneven surface against which the valve is expanded outward is created. This irregularity creates sizing problems, and also may adversely affect the circularity of the expanded valve which negatively affects the valve efficacy by impairing leaflet coaptation.

Despite some advances in MIS valve design, there remains a need for a valve that can be constricted into a smaller package without damaging the biological valve within, and which can be reliably expanded generally into a tube against the relatively uneven surface of the annulus or annulus and intact native leaflets.

SUMMARY OF THE INVENTION

The present invention provides an expandable prosthetic heart valve for placement in a host heart valve annulus, comprising a stent body that is rolled into a compact configuration, implanted, then unrolled into a tubular shape and secured into place in the valve annulus. The valve is small enough in its contracted state to be passed down a percutaneous or endovascular delivery tube, thus avoiding the need for open heart surgery. Flexible membranes attach around the inner wall of the stent body, preferably inward of sinus apertures, and have sufficient play to billow inward into contact with one another and form the occluding surfaces of the one-way valve. The stent may be one or two pieces, and the delivery and implantation may occur in one or two steps using one or two delivery tubes.

In accordance with the present invention, a rolled prosthetic heart valve suitable for minimally invasive delivery and implantation in a heart valve annulus is provided. The heart valve comprises a stent body that has a generally tubular shape set and is structured to be rolled into a spiral sized to pass through a patient's vasculature. A plurality of flexible membranes fastened to the inside of the stent body to form occluding leaflets of the heart valve.

In one embodiment, the stent body is adapted to conform to a first, contracted configuration in which the stent body is spirally rolled about an axis, and a second, expanded configuration in which the stent body is substantially unrolled and at least partly forms a tube centered about the axis and sized to engage an annulus of a patient's heart valve. At least one guide may be provided to insure the stent body expands evenly along the axis during a conversion between the first, contracted configuration to the second, expanded configuration. Further, the stent body may define a pair of opposed side edges that generally mate in the second, expanded configuration, and a pair of opposed end edges that extend between the side edges, wherein the guide comprises a tab extending generally radially along each one of the end edges.

The stent body desirably forms the only rolled structure in the heart valve. In one embodiment, the stent body has an annulus section on an inflow end, a sinus section, and an outflow section. The sinus section is between the annulus section and outflow section and has a plurality of sinus apertures outward of each membrane. There may be three generally semi-circular sinus apertures and three separate membranes fastened around the edge of each except on one side which forms a free edge of each leaflet. The outer edge of each membrane is preferably folded over and fastened to an inner surface of the stent body adjacent an edge of the associated sinus aperture.

In accordance with a further aspect of the invention, a prosthetic heart valve suitable for minimally invasive delivery and expansion against a heart valve annulus is provided. The valve includes a stent body that has a first, contracted configuration with a first diameter for delivery through the vasculature of a patient and a second, expanded configuration with a predetermined maximum second diameter regardless of the size of the heart valve annulus. The stent body may be a sheet-like member having a generally tubular shape and adapted to be rolled into a spiral sized to pass through a patient's vasculature. Desirably, the stent body has a plurality of sinus apertures and the heart valve further includes a plurality of flexible membranes fastened around the sinus apertures to form occluding leaflets of the heart valve. The heart valve may further include at least one anchoring element comprising a curved strip extending radially outward from the stent body designed to prevent axial migration of the heart valve after implantation in the annulus.

The stent body may be adapted to conform to a first, contracted configuration in which the stent body is spirally rolled about an axis, and a second, expanded configuration in which the stent body is substantially unrolled and at least partly forms a tube centered about the axis and sized to engage an annulus of a patient's heart valve. The tube has a pair of end edges, wherein the stent body has a pair of opposed side edges that mate in the second, expanded configuration. The stent body further includes lockout structure to retain the opposed side edges in mating engagement and define the predetermined maximum second diameter. The lockout structure may comprise tabs formed on both of the end edges and adjacent one of the side edges, and slots formed in both of the end edges adjacent the other of the side edges that are sized to receive and retain the tabs. Alternatively, the lockout structure both defines the predetermined maximum second diameter thus preventing further expansion of the stent body, and prevents contraction from the expanded tubular shape.

Another aspect of the invention is a method of prosthetic heart valve implantation. The method involves positioning a rolled prosthetic heart valve at a heart valve annulus, and unfurling the prosthetic heart valve from a spirally-wound contracted, first configuration to an unwound expanded, second configuration at the annulus. Desirably, the prosthetic heart valve comprises a single stent body having a plurality of flexible, biocompatible membranes incorporated therein that form heart valve leaflets in the expanded configuration. The method also may include further including anchoring the prosthetic heart valve in its expanded configuration to the heart valve annulus. The native heart valve leaflets of the heart valve annulus may be left in place and the step of unfurling causes the prosthetic heart valve to contact and outwardly compress the native leaflets. The step of unfurling further may include ensuring that the prosthetic heart valve remains generally tubular. The prosthetic heart valve may be locked in its expanded configuration.

In a preferred embodiment, a prosthetic heart valve of the present invention suitable for minimally invasive delivery comprises a generally sheet-like stent body and a plurality of flexible, biocompatible membranes incorporated into the stent body to form heart valve leaflets. The stent body has a first, contracted configuration in which it is spirally-wound about an axis such that at least one winding of the stent body surrounds another winding. The stent body further has a second, expanded configuration in which it is substantially unwound and at least partly forms a tube centered about the axis and sized to engage an annulus of a patient's heart valve. In accordance with one aspect, the stent body comprises a primary stent coupled to a secondary stent that at least partially fits within the primary stent. The flexible, biocompatible membranes are incorporated into the secondary stent. Alternatively, the stent body is formed of a single stent.

The prosthetic heart valve may comprise a single stent body having a plurality of flexible, biocompatible membranes incorporated therein that form heart valve leaflets in the expanded configuration. Alternatively, the prosthetic heart valve comprises a two-piece stent body with a primary stent and a secondary stent, wherein the steps of delivering and unfurling comprise delivering and unfurling the primary stent first and then delivering and unfurling the secondary stent within the primary stent. The secondary stent may be guided into coupling position within the primary stent using one or more guidewires. The method further may include anchoring the prosthetic heart valve in its expanded configuration to the heart valve annulus. With a two-piece embodiment the primary stent is anchored to the annulus and the secondary stent anchored to the primary stent. If the native heart valve leaflets of the heart valve annulus are left in place, the step of unfurling causes the prosthetic heart valve to contact and outwardly compress the native leaflets. The step of unfurling further may include ensuring that the prosthetic heart valve remains generally concentric about a single axis, and also locking the prosthetic heart valve in its expanded configuration.

A further understanding of the nature and advantages of the invention will become apparent by reference to the remaining portions of the specification and drawings.

BRIEF DESCRIPTION OF THE DRAWINGS

FIGS. 2A-2D are various plan and perspective views of a heart valve stent of the present invention shown flattened prior to a final fabrication step;

FIGS. 3A and 3B are schematic views of an exemplary heart valve deployment system of the present invention utilizing cables around the heart valve stent to regulate its expansion;

FIGS. 4A-4F are various perspective views of an alternative heart valve stent of the present invention having gear tracks and shown without flexible membrane leaflets attached, the stent shape has been fabricated with a tubular shape set but has not had its side edges locked together to form a closed tube;

FIGS. 6A-6C are perspective views of a heart valve stent of the present invention similar to the one in FIGS. 2A-2D and shown rolled up into a relatively tight spiral to illustrate how a locking/alignment mechanism functions;

FIGS. 7A-7C are perspective views of the heart valve stent of FIGS. 6A-6C again rolled into a spiral and illustrating how a locking/alignment tab on an outer winding engages the immediately adjacent winding;

FIGS. 8A-8B are perspective views of an exemplary heart valve deployment system for use with the stent seen in FIGS. 4 and 5;

FIGS. 10A-10D are different perspective views of a primary stent for use in a two-piece expandable heart valve of the present invention;

FIG. 11 is a plan view of an exemplary secondary stent for use in a two-piece expandable heart valve of the present invention, illustrating body tabs and slots for alignment during unrolling;

FIG. 12 is a partial perspective view of a commissure/junction region of an exemplary secondary stent, particularly illustrating side tabs for alignment during unrolling;

FIGS. 15A-15H are perspective views of an exemplary mandrel for setting the shape of a heart valve stent of the present invention, in various stages of the operation.

DESCRIPTION OF THE PREFERRED EMBODIMENTS

Figure 1:
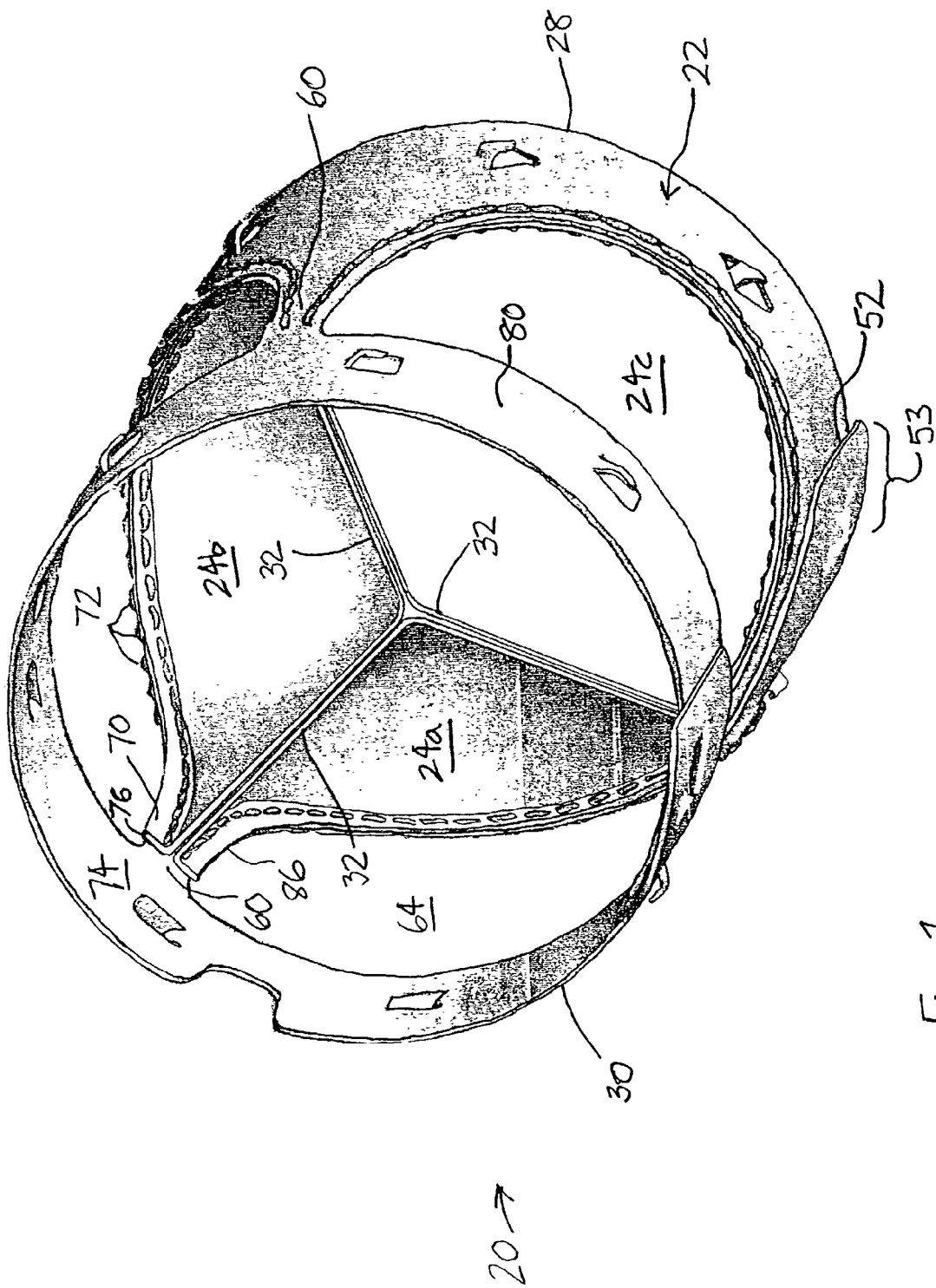
FIG. 1 is a perspective view of a an exemplary one-piece expandable heart valve of the present invention as viewed from the outflow end.

The present invention discloses a number of expandable heart valves for implantation in a host annulus, or host tissue adjacent the annulus. The valves may be implanted in any of the four valve positions within the heart, but are more likely to be used in replacing the aortic or mitral valves because of the more frequent need for such surgery in these positions. The patient may be placed on cardiopulmonary bypass or not, depending on the needs of the patient.

Although the present invention is illustrated with self-expandable rolled heart valves, those of skill in the art will recognize that certain features may be useful for plastically deformable rolled heart valves. Moreover, the invention described herein embodies certain features that may be adapted to be used with minimally-invasive heart valves other than the rolled type. For example, the configuration that the valve expands to a fixed diameter is useful for all valves, not just the rolled type.

A number of expandable prosthetic heart valves are disclosed that are initially rolled into a tight spiral to be passed through a catheter or other tube and then unfurled or unrolled at the implantation site, typically a valve annulus. The heart valves comprise one- or two-piece stent bodies with a plurality of leaflet-forming membranes incorporated therein. Various materials are suitable for the stent body, although certain nickel-titanium alloys are preferred for their super-elasticity and biocompatibility. Likewise, various materials may be used as the membranes, including biological tissue such as bovine pericardium, or synthetic materials. It should also be noted that specific stent body configurations disclosed herein are not to be considered limiting, and various construction details may be modified within the scope of the invention. For example, the number and configuration of lockout tabs (to be described below) may be varied.

Those of skill in the art will recognize that the means and techniques for delivering and implanting the prosthetic heart valves disclosed herein are numerous and not the specific focus of the present application. In general, the heart valves in a first, contracted configuration are delivered through a tube such as a percutaneously-placed catheter or shorter chest cannula and expelled from the end of the tube in the approximate implantation location. The heart valve is then expanded via a balloon, mechanical means, or self-expanded from internal elastic forces, into a second, expanded configuration that engages the native host tissue, such as the target valve annulus. Depending on the native valve being replaced, the prosthetic heart valve may have varying axial lengths. For example, in the aortic position, a portion of the valve may extend upward into and even contact the aorta to better stabilize the commissure regions of the valve. In other words, the particular design of the valve may depend on the target valve location.

The present application claims priority from both U.S. application Ser. No. 09/815,521, entitled "ROLLED MINIMALLY-INVASIVE HEART VALVES AND METHODS OF USE," filed Mar. 23, 2001, and U.S. application Ser. No. 09/951,701, entitled "METHODS AND APPARATUSES FOR DEPLOYING MINIMALLY-INVASIVE HEART VALVES," filed Sep. 13, 2001. The disclosures of both these prior applications are expressly incorporated herein by reference.

With reference to FIG. 1, an exemplary one-piece prosthetic heart valve 20 of the present invention is shown. The valve 20 basically comprises a stent body 22 and a plurality of leaflet-forming membranes 24a, 24b, and 24c. The stent body 22 is shown in its expanded configuration generally defining a tube centered about an axis. The membranes 24 fasten within the stent body 22 so as to form a one-way valve therewithin, and orient the valve to have an inflow end 28 and an outflow end 30. In a preferred embodiment, there are three such membranes 24a, 24b, 24c each having a free edge 32 that extends inward from the stent body 22 and coapts or meets the other two free edges generally along radial lines spaced apart 120° with respect to each other to close the valve during the back flow cycle of blood flow. When blood flows in the opposite direction, from the inflow to the outflow end, the free edges 32 of the membranes 24 move radially outward away from each other to open the valve. It should be understood that there may be two or more leaflets, though three takes advantage of the natural sinuses and their effect on blood flow to close the leaflets.

FIGS. 2A-2D illustrate a stent body 22 that is similar to the stent body 22 shown in FIG. 1 incorporated into the valve 20. There are many common elements of these two stents 22, 22, with the primary difference being the anchoring barbs, as will be explained. FIGS. 2A-2D will be referenced to explain the features of the stent, most of which can also be seen in FIG. 1, with the same reference numbers used to identify common elements of the two versions.

The tubular stent body 22 comprises three sections, starting at the inflow end 28 and moving toward the outflow end 30: an annulus section 40, a sinus section 42, and an outflow section 44. The three sections 40, 42, and 44 are desirably formed from a single generally sheet-like piece of material that can be cohesively rolled into a tight spiral and expanded into the tubular configuration shown. In this regard, the stent body 22 includes an axially-oriented first side edge 50 that mates with an axially-oriented second side edge 52 along a longitudinal seam 53. The two side edges 50, 52 abut or overlap and lock together using cooperating tabs and slots, as will be described below.

In a preferred implantation technique, the prosthetic heart valve 20 expands outward and compresses against the native leaflets which present a relatively uneven base. Even if the leaflets are excised, the circularity of the annulus depends on the skill of the surgeon. Minimizing any openings in the annulus section 40 enhances its rigidity so as to ensure a relatively tubular support structure for the leaflet-forming membranes 24. However, anchoring elements 56 may be provided in the annulus section 40, and may be formed by integrally cut slits as shown. In addition, apertures or thinned regions may be provided in the side wall of the tubular stent body 22, as will be described in more detail below, including the annulus section 40, to reduce the roll-up stiffness of the stent 22.

With reference to FIGS. 2A and 2B, the sinus section 42 comprises a plurality (preferably three) of generally axially extending commissures 60 and curvilinear cusps 62 defined by relatively large sinus apertures 64 in the stent body 22. In the illustrated embodiment, the sinus apertures 64 are generally semi-circular with a straight, circumferential edge 66 defined by the beginning of the outflow section 44. A plurality of small attachment apertures 68 track along the edges of the sinus apertures 64, extending around the curvilinear cusps 62 and up to the top of each commissure 60.

Sutures or similar expedient fasten the membranes 24 to the stent body 22 using the generally semi-circular rows of attachment apertures 68. More particularly, as seen in FIG. 1, an outer edge portion 70 of each membrane 24 folds to lie against an inner surface 74 of the stent body 22, along the cusps 62 and commissures 60. This folded attachment helps reduce localized stresses caused by the sutures through the membrane 24, and enhances coaptation of the free edges 32 at the commissures 60. Fasteners such as sutures 72 secure the outer edge portion 70 flush against the inner surface 74. The sutures typically loop through the membrane 24 twice at each attachment aperture 68 in a single mattress stitch, though various other stitching techniques are known. In a preferred embodiment, the attachment apertures 68 are spaced apart a minimum distance of about 0.004-0.0075 inches for strength.

As seen in FIG. 1, a small lip 76 of the outer edge portion 70 of each membrane 24 desirably projects beyond the sinus aperture 64 to help protect the membrane 24 from rubbing directly against the material of the stent body 22 during operation of the valve. That is, there is membrane-to-membrane cushioned contact at the sinus apertures 64 when the membranes 24 are forced outward in the opening cycle of the valve. Additionally, all exposed edges of the stent body 22 are electropolished or coated with a layer of lubricious material (e.g., AAA-SurModic or TEFLON) to eliminate any sharp corners and thus reduce wear on the flexible membranes 24.

The free edge 32 of each membrane 24 meets the stent body 22 at one of the commissures 60. Because adjacent arrays of attachment apertures 68 converge in the outflow direction along each commissure 60, the free edges 32 of adjacent membranes 24 coapt at or closely adjacent to the stent body inner surface 74, as seen in FIG. 1. This configuration eliminates leakage between the free edges 32 when the valve closes.

The outflow section 44 desirably comprises a circular band 80 of material that joins the outflow ends of the commissures 60. The outflow section 44 may not be in contact with any tissue of the heart, but rather may project into the respective outflow chamber as a support for the three commissures 60. That is, substantial inward radial loads are imposed on the commissures 60 during the closing cycle of the valve, and the outflow section 44 maintains the spacing between the commissures to ensure proper coaptation of the free edges 32 of the membranes 24.

With reference again to FIGS. 2A-2D, the stent 22 includes structure for both coupling the two side edges 50, 52 together at the seam 53, and for helping maintain the stent in a tubular, rather than a frustoconical, configuration during expansion. As will be seen below, with an alternative embodiment of the stent, these two functions can be performed by separate structure. However, features on the stent 22 perform both these functions.

More specifically, as seen in FIG. 2B, a locking slot 82 is formed in each of the end edges 20, 30 adjacent the first side edge 50. On the other end of the stent 22, a locking/alignment tab 84 is formed as a cutout of the stent body on each side thereof, adjacent the second side edge 52. Although not shown, these tabs 84 are bent so as to extend parallel to but not in the plane of the rest of the stent 22. That is, each tab 84 bends radially inward approximately along a line so that they connect with the rest of the stent body. The stent 22 in FIGS. 2A-2D is shown flat prior to having its tubular shape set and prior to a final forming step wherein the tabs 84 will be properly bent. A pair of notches 86 are formed in the stent 22, one in each of the inflow and outflow ends 28, 30.

Interaction between the slots 82, tabs 84, and notches 86 will be described below with reference to similar features on an alternative valve stent. In addition, an exemplary sequence of manufacture of a valve stent of the present invention will be described below in more detail.

The final shape of the anchoring elements 56 are not shown in these figures. In the illustrated embodiment, there are seven anchoring elements 56 each formed by a pair of parallel slits in the stent 22. The strip of material between the slits will be bent radially outward in an arcuate shape so as to form partial rings or loops. Because the edges of the anchoring elements 56 face in the axial direction, they provide adequate frictional resistance to migration of the heart valve once implanted. Furthermore, the convex outer contour of these anchoring elements 56 avoids undue damage to the surrounding tissue.

The stents 22 seen in FIGS. 1-2D are representative of a number of similar stents that are self-expandable and are deployed simply by placing them in an implant position and releasing any restraints. FIGS. 3A-3B schematically illustrate one system for deploying a heart valve having a stent such as those shown in FIGS. 1-2D. FIG. 3A illustrates a heart valve 90 shown in a contracted or roll-up configuration, while FIG. 3B shows the valve after having been expanded or unrolled. It should be noted that the flexible membranes or leaflets are not illustrated in these Figs. to facilitate understanding of how the valve is deployed.

As seen in FIG. 3B, the valve 90 is mounted on the distal end of a delivery catheter 92, and specifically over an expansion balloon 94. The delivery catheter 92 has a distal mouth 96 from which extend smaller catheters that operate the balloon 94 and help regulate the self-expansion of the valve 90. Specifically, a first catheter 98 extends into the middle of the balloon 94 and provides a path for a guidewire 100 and also an inflation lumen. A second catheter 102 extends from the delivery catheter mouth 96 and bends slightly radially outward into alignment with an outermost winding of the heart valve 90. The reader will notice that the catheter 102 bends only slightly outward when the valve 90 is in its contracted configuration as seen in FIG. 3A, while the catheter bends slightly further outward after expansion of the valve as seen in FIG. 3B. Therefore, the catheter 102 must have sufficient flexibility so as to flex upon expansion of the valve 90 without unduly interfering with expansion thereof.

The second catheter 102 houses a flexible elongated cable sheath 104 from which a pair of cables 106a, 106b emerge at opposite ends of the valve 90. These cables 106a, 106b encircle the valve 90 and provide a control on the expansion thereof. That is, the cables 106a, 106b enter windows 108 along the cable sheath 104 and extend in a proximal direction therethrough to the proximal end of the delivery catheter 92. The cables 106a, 106b slide easily within the cable sheath 104 and thus can be gradually paid out as the valve 90 expands. For instance, the cables 106a, 106b are shown in FIG. 3A having a relatively small circumference around the contracted valve 90, while FIG. 3B shows the cables having been pulled through the windows 108 along with the expanded valve. In this manner, the operator can gradually release the cables 106a, 106b after the heart valve 90 is in position and any other restraints removed so as to govern the expansion of the valve and prevent any problems associated with too rapid an expansion. The shaped expansion balloon 94 may also be used to help urge the valve open, but is typically relied upon to perform the final bit of expansion and "lock" the valve into its desired tubular size. The valve 90 is sized so that it is slightly larger than the measured host annulus. Therefore, the balloon 94 is required to overcome the last portion of expansion after the stent of the valve contacts the surrounding tissue.

FIGS. 4A-4F and FIGS. 5A-5F illustrate an alternative heart valve stent 120 of the present invention that incorporates a pair of gear tracks for engagement with a deployment mechanism having gear teeth. Such a heart valve stent and deployment mechanism were disclosed in U.S. application Ser. No. 09/951,701. The heart valve stent 120 incorporates features described above with reference to the stent 22; namely, the stent 120 includes similar features for locking the stent open, ensuring concentric tubular expansion, and anchoring the stent within the host annulus.

The stent 120 is illustrated in FIGS. 4A-4F in its relaxed fully formed tubular shape prior to being locked out, while FIGS. 5A-5F show the stent after having been locked out. As will be described below, the stent has a tubular shape that has been set, through processing over a period of time, in a special mandrel. The stent 120 assumes the shape in FIG. 4A when relaxed. And thus when locked out, as in FIG. 5A, has an outward bias. This bias ensures that the stent 120 tends to expand in the absence of external restraints.

As in the earlier embodiments, the stent 120 has an inflow end 122, an outflow end 124, and pair of side edges 126, 128 that come together to form the locked out valve. As seen in FIG. 4B, the stent 120 includes an inflow section 130, a sinus section 132, and an outflow section 134. A plurality, preferably three, sinus apertures 136 (see FIG. 4C) in the sinus section 132 receive the flexible membranes in the same manner as described above with respect to FIG. 1. That is, the membranes are attached around the curvilinear portion of the apertures 136 with free edges toward the outflow section 134.

As mentioned above, a pair of gear tracks 140a, 140b is provided in both the inflow section 130 and the outflow section 134. The gear tracks 140a, 140b each comprise a circumferential series of generally rectangular openings that receive gear teeth of a deployment mechanism as seen in FIGS. 7A-7D, and also in the prior application Ser. No. 09/951,701. Each of the tracks 140a, 140b extends from the first, inner side edge 126 approximately 60% around the circumference of the stent and terminates just short of engagement notches 142a, 142b (see FIG. 4A) opening in both the inflow and outflow ends 122, 124.

As seen best in FIGS. 4D and 4F, the stent 120 includes a pair of guide tabs 150a, 150b adjacent to the second side edge 128 that engage a pair of lockout slots 152a, 152b adjacent the first side edge 126. With reference to FIG. 4F, each guide tab 150 comprises a cantilevered section of the stent body that is formed by a generally U-shaped cut-out 154. The free end of the tab 150 lies inward from the adjacent end of the stent 120 (the inflow end 122 in FIG. 4F) and the tab is bent to ultimately lie parallel to, but inward from, the adjacent stent body. With reference to FIG. 4C, the first side edge 126 comprises a pair of strip-like extensions 156 on either side of a recessed portion 158. Because the second side edge 126 comprises the inner edge of the wound valve, it forms the smallest radius. Therefore, the extensions 156 are provided to reduce the stresses in the material because of the small radius.

Figure 5A:
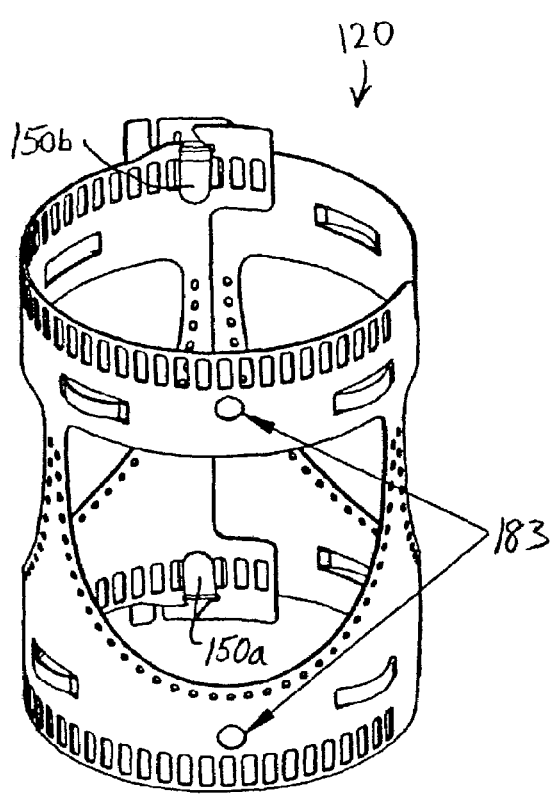
FIGS. 5A-5F are various perspective and plan views of the heart valve stent of FIGS. 4A-4F shown with its side edges locked together to form a complete tube.
Figure 5B:
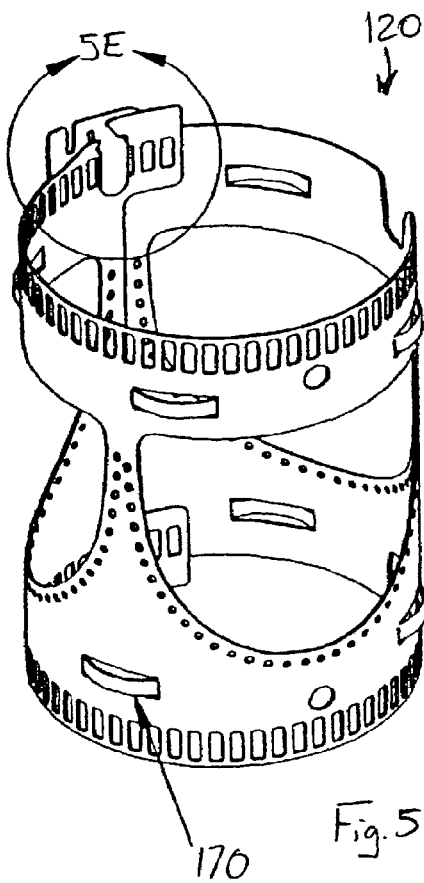
Figure 5E:
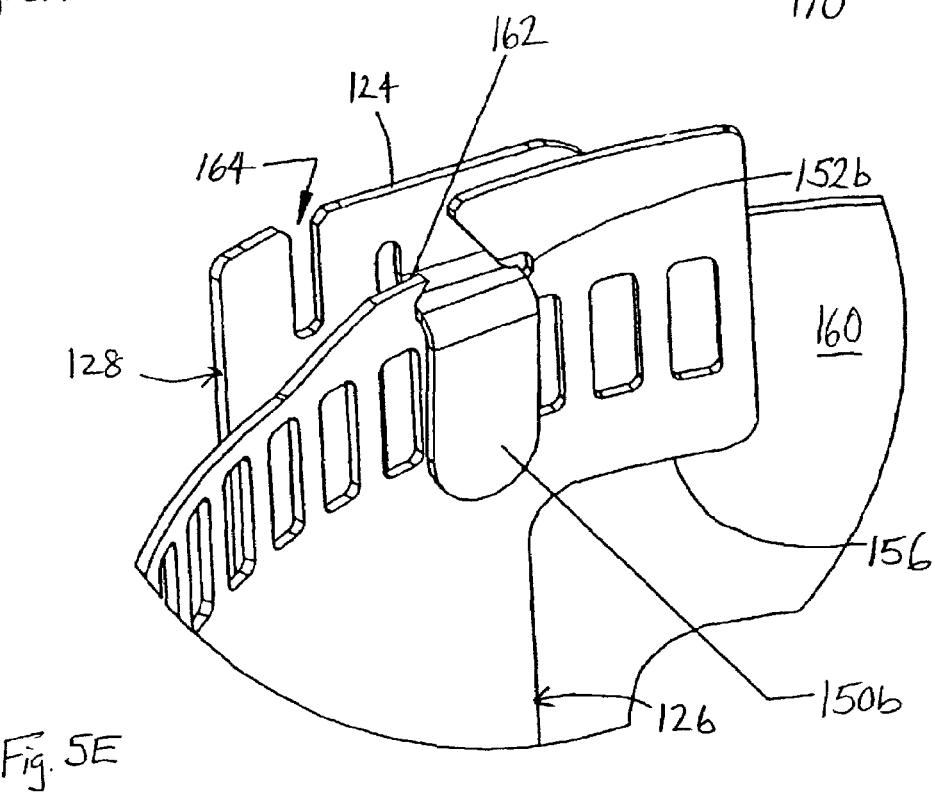
Figure 5C:
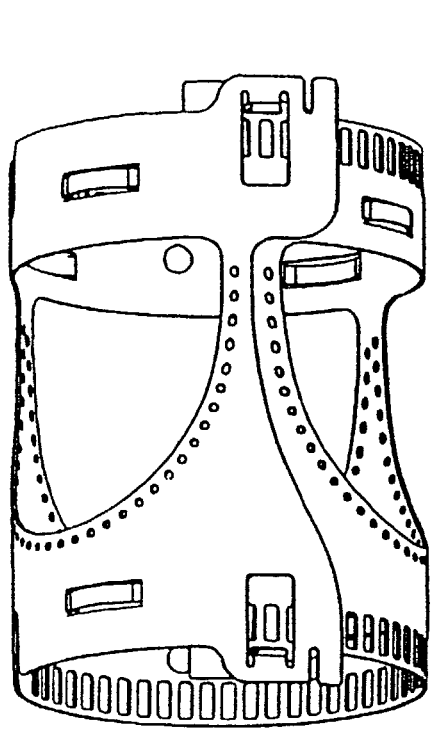
Figure 5D:
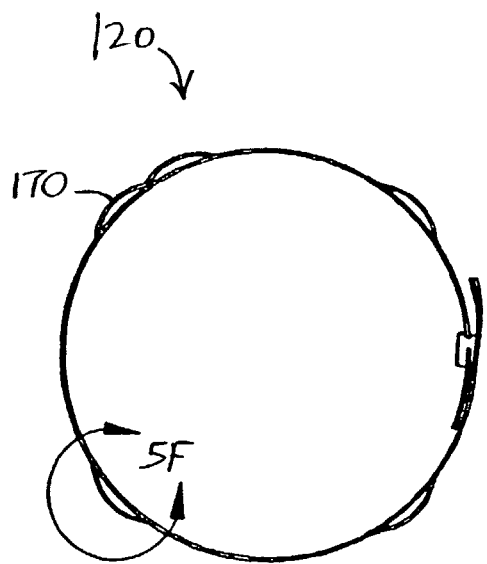

Now with reference to FIGS. 5B and 5E, the interaction between the two side edges 126, 128 of the stent 120 is detailed. The strip-like extension 156 is seen passing between the guide tab 150b (this time on the outflow end of the stent 120) and the inner surface 160 of the stent. The bend of the guide tab 150b fits closely into the lockout slot 152b. A small tooth 162 on one side of the slot 152b prevents the guide tab 150b from disengaging the slot. In this manner, the two side edges 126, 128 on both ends of the stent are locked together. Advantageously, there is only one open or expanded diameter of the stent 120 by virtue of the locking side edges 126, 128. Specifically, the guide tabs 150a, 150b slide into and are captured by the lockout slots 152a, 152b such that the stent 120 assumes a predetermined and fixed dimension. This is an improvement over existing MIS heart valves that rely on a conventional tubular stent or similar expedient for a framework. In those types of valves, a balloon is typically used for expansion and resistance from the surrounding annulus may vary the final diameter. Therefore, the present invention is believed to be the first disclosure of an expandable prosthetic heart valve having a predetermined maximum diameter.

FIG. 5E also illustrates a small axial slot 164 formed in the outflow end 124 near the second side edge 128. This slot 164 engages a feature on a geared deployment mechanism used to deploy the valve stent 120, as seen for example in FIGS. 8A-8B.

Figure 5F:
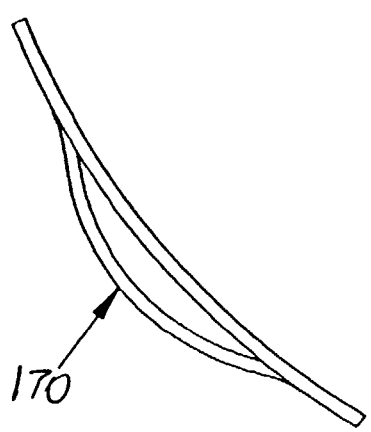

FIG. 5F is a detail of the shape of one of a plurality of anchoring elements 170 provided in the stent 120. As described above with respect to the stent 22 of FIG. 2A, the anchoring elements 170 each comprise a small strip of the stent 120 defined therein by a pair of parallel slits. During the stent formation process these strips are bent radially outward from the remainder of the stent body into the curved shape shown. Again, because the edges of this curved strip face in the axial directions, they effectively anchor the valve and prevent it from migrating. Moreover, the curved shape of the elements 170 reduces the chance of snagging other portions of the stent 120 during unrolling.

FIGS. 4A-4F also illustrate a means to reduce the bending stress at locations around the stent 120 to either prevent failure or even the stiffness of the stent along any one location around its circumference. The former result is attained, as seen in FIG. 4F, by forming a region 180 of the extensions 156 on the first side edge 126 to be thinner than the rest of the body of the stent 120. Because the extensions 156 form the innermost portion of the spirally wound valve stent 120, they are curled into the smallest radius. By removing material from the outer surface of the extensions 156, the area moment of inertia in bending at that location is reduced, thus reducing the bending stresses in the material. For example, the thickness of the material may be between 0.1-0.3 mm (0.0039-0.012 inches), and desirably about 0.19 mm (0.0075 inches). The thinned region 180 has between 25%-50% of the thickness is removed, and desirably between 40%-50%. For example, where the stent thickness is 0.19 mm (0.0075 inches), about 47% or 0.089 mm (0.0035 inches) is removed to reduce the bending stress.

Furthermore, FIGS. 4A-4B illustrate thinned generally triangular regions 182 in the body of the stent 120, specifically toward the inflow end in the areas between the sinus apertures 136, having the most material. It is at these locations where the stiffness of the stent is greatest. By removing material from the exterior surface of the stent, such as by chemical etching, bending stresses are reduced at those locations. As with the extensions 156, between 25%-50% of the thickness is removed, and desirably between 40%-50%. Of course, rather than only thinning the material, bend relief apertures that open all the way through the stent wall may be provided, as will be illustrated below with respect to another stent embodiment.

FIGS. 4A-4D and 5A-5C, show a pair of tooling holes 183 formed in the stent 120 that mate with pins on a tooling mandrel described below. The stent 120 is initially a flat blank and is set into the tubular shape shown by the mandrel. The holes 183 receive the tooling pins to accurately locate the stent within the mandrel.

FIGS. 6A-6C illustrate a stent 184 which is similar to the stent 22 described with perspective to FIGS. 1 and 2A-2D in that it has no gear tracks, and which also has the lockout/alignment tabs/slots as described with respect to all of the previously described embodiments. These figures illustrate how the tabs and slots become engaged.

FIGS. 6A-6C show the stent 184 rolled up into a relatively tight spiral but prior to engagement of the tabs 186 with the adjacent coil of the stent. The detail of FIG. 6C illustrates the guide tab 186 aligned with engagement notches 188 in the immediately adjacent stent winding. The notches 188 are substantially the same as the notches 142a, 142b described above with respect to FIGS. 4A-4F. A locked slot 190 that will eventually engage and hold the tab 186 as seen on the inner winding of the valve stent 184. Because the tab 186 lies radially inward from its base winding, it falls into the engagement notch 188 as shown.

Now with reference to FIGS. 7A-7C, the stent 184 is shown after having been permitted to uncoil slightly such that the tabs 186 slide underneath the immediately adjacent winding. With reference back to FIG. 2D, the illustrated tabs 84 pass through the notches 86 and slide along the stent body all the way to the corresponding lock slot 82. Likewise, as the stent 184 in FIGS. 7A-7C unwinds, the tabs 186 slide underneath the immediately adjacent winding and eventually become engaged with the lock slots 190. Because there are two side tabs 186 on each outside winding of the stent 184 that ride over the next inner winding, the stent uncoils concentrically in a tube rather than unevenly in a cone. That is, these tabs 186 are spaced a certain distance apart approximately equal to the stent length from inflow to outflow, and any misalignment of the coiled stent as it unwinds will be resisted because it would tend to spread the two tabs apart on a diagonal. Therefore, because two adjacent windings are aligned, the rest of the windings are also held aligned. There are other ways of maintaining alignment as described elsewhere herein.

FIGS. 8A-8B illustrate a deployment mechanism 192 having a gear shaft 194 and a pair of sets of gear teeth 196 thereon engaging the stent 120 of FIGS. 4 and 5. The deployment mechanism 192 includes a pair of end keepers 198 that engage a portion of the stent 120 and permit the gear teeth 196 to engage the gear tracks 140a, 140b. The deployment mechanism 192 is illustrated schematically, and can be seen in greater detail in co-pending application Ser. No. 09/951,701.

Figure 9:
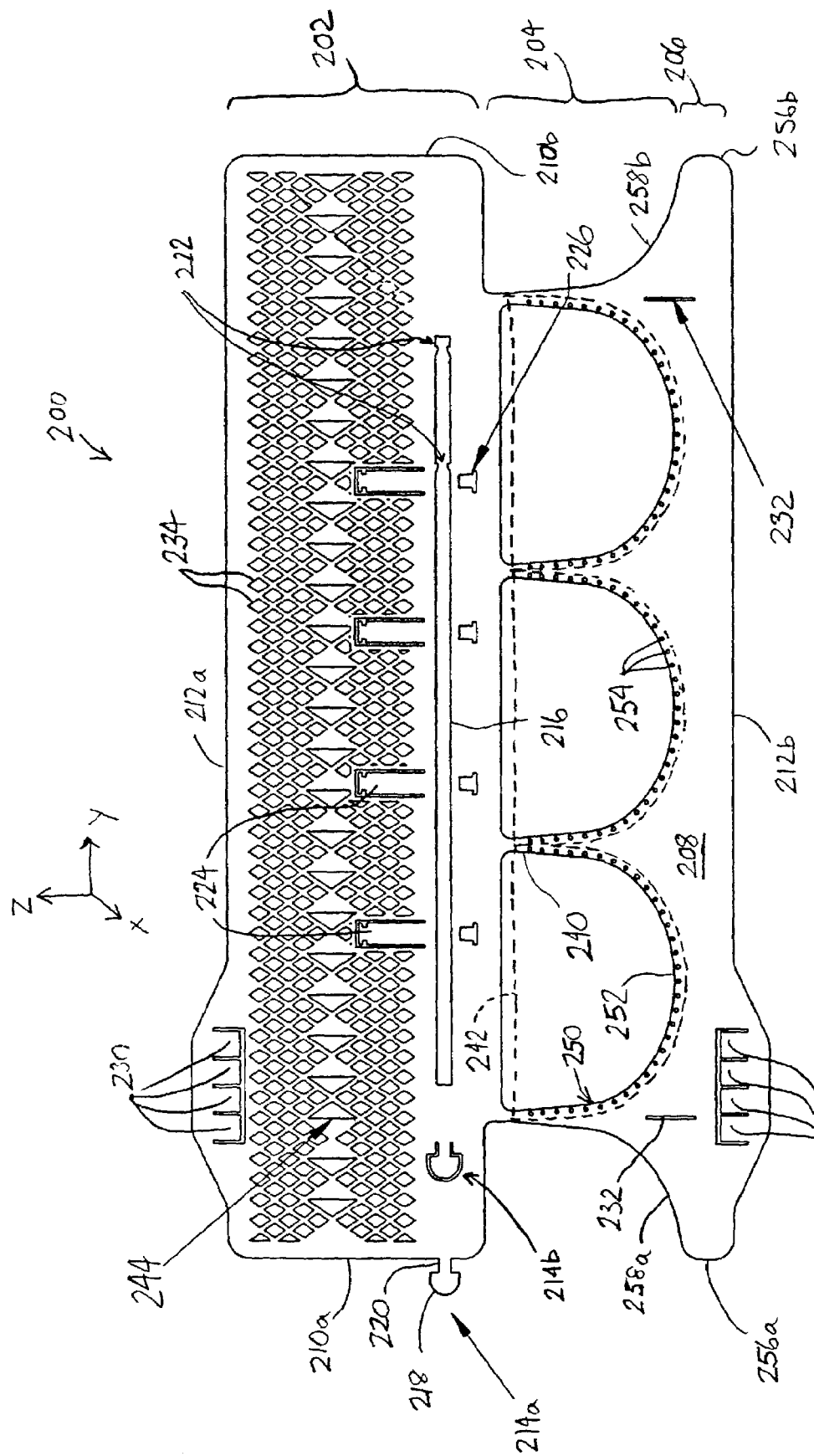
FIG. 9 is a plan view of another alternative one-piece expandable heart valve stent of the present invention having a long outflow section.

FIG. 9 illustrates a still further one-piece expandable heart valve stent 200 of the present invention in its flattened configuration having a somewhat more solid or robust outflow section 202 than shown previously, coupled to a sinus section 204 and an annulus section 206 on the inflow end of the stent. The stent 200 comprises a single sheet-like body 208 of a rolled superelastic metal alloy, preferably Nitinol. For orientation purpose, the body 208 is initially formed in the Y-Z plane as shown, and is elongated in the Y direction with a generally rectangular outline. The body 208 is designed to be rolled up on itself about a Z-axis into a relatively tight spiral, and later unrolled to form a tube with a first side edge 210a connecting to a second side edge 210b. In the illustrated embodiment, the left side of the stent body 208 forms the inner winding of the spiral while the right side is the outer winding. Desirably, and as mentioned above, the first side edge 210a and second side edge 210b overlap in the enlarged tubular configuration. The body 208 also defines relatively linear first and second end edges 212a, 212b that form the circular outflow and inflow rims, respectively, of the tubular stent.

The stent 200 includes alignment structure for ensuring proper unrolling about the central Z-axis, and also locking structure for maintaining the final tubular shape. Specifically, a pair of guide/lockout tabs 214a, 214b engage a guide slot 216 that extends along the Y-axis in the outflow section, closely adjacent the sinus section 204. A single such guide slot 216, as shown located generally in the center of the body 208 with respect to the Z-axis, is believed sufficient to hold the stent in the final tubular shape, although two or more may be used as described previously. The guide/lockout tabs 214a, 214b each include an enlarged generally semi-circular head 218 and a narrow neck 220 connecting the head to the body 208. A first tab 214a extends from the first end edge 210a while a cutout in a mid-portion of the body 208 forms a second tab 214b.

The spaced tabs 214a, 214b align with the guide slot 216 and are annealed out of the plane of the body 208 so as to fit within the slot. Specifically, the tabs 214a, 214b are annealed so that they bend inward with respect to the rolled spiral of the stent body 208 and can then be introduced into the slot 216. Once in the slot 216, the head 218 of each tab 214a, 214b projects through to the outside of the body 208 and retains the tabs in engagement with the slot. The neck 220 has a width that is slightly smaller than the slot width for easy longitudinal movement therewithin. As the stent body 208 unfurls from its tightly coiled contracted state to its expanded state, the tabs 214a, 214b travel along the slot 216 (from the left to the right in the drawing). As this process occurs, the maintenance of the tabs 214a, 214b within the slot 216 ensures that the stent body 208 will not misalign and unroll into a conical shape. Ultimately, the tabs 214a, 214b travel past two pairs of similarly spaced lockout notches 222 annealed out of the plane of the body 208 toward the inside of the now tubular stent. The interference between these lockout notches 222 and the heads 218 of the tabs 214a, 214b retains the stent 200 in its open, expanded configuration.

A plurality of engaging pairs of bridge tabs 224 and apertures 226 maintain a uniform width of the guide slot 216 to retain the tabs 214a, 214b therein during unrolling of the stent body 208. Each tab 224 is annealed so as to bend and lock into the corresponding aperture 226. Maintenance of the guide slot 216 width ensures a continuous engagement of the tabs 214a, 214b and guide slot 216 during the unrolling process.

The stent body 208 further includes a plurality of edge tabs 230 located along both end edges 212a, 212b adjacent the first side edge 210a. Although shown flattened in the plane of the stent body 208, the edge tabs 230 are also annealed to bend generally perpendicular to the stent body. The edge tabs 230 are disposed closely to and constrain the end edges 212a, 212b during the unrolling process to further help prevent misalignment. A pair of stop slots 232 is formed in the anchor section 206 to limit the extent that the stent body 208 unrolls. One side of each slot 232 is annealed out of the plane of the stent body 208 so that they engage each other after the body has unrolled to the tubular final shape.

The outflow section 202 includes an array of apertures 234 forming an open lattice, mesh or grid pattern that reduces the stent surface area and thus the risk of thrombosis after implantation. The open mesh pattern is somewhat stiffer than, for example, the grid pattern shown in the stent of FIG. 1, and helps stabilize the valve commissures 240 about which flexible leaflet membranes 242 (shown in phantom) are attached. A plurality of triangular-shaped cutouts 244 aligned in the Y-direction in the outflow section 202 "ratchet" against one another during unrolling of the stent body 208 and thus incrementally prevent closing of the stent.

Still with reference to FIG. 9, the sinus section 204 incorporates three membrane apertures 250 defining the aforementioned commissures 240 and intermediate curvilinear cusps 252. A series of attachment holes 254 closely surrounds each aperture, 250 and is used to suture or otherwise attach each membrane 242 to the stent 200. The edge of each membrane 242 is folded as described above with respect to FIG. 2B to help prevent wear and ensure longevity. The opposed ends of the sinus section 204 are shaped to conform to the outer two membrane apertures 250. That is, a pair of opposed extension flaps 256a, 256b on the annulus section 206 overlap, each of which transitions along a curvilinear edge 258a, 258b toward the outflow section 202. These curvilinear edges 258a, 258b provide reliefs to avoid occluding either of the outer two membrane apertures 250 when the stent is locked open and the flaps 256a, 256b overlap.

Although not shown, a plurality of anchoring barbs are desirably provided in at least the annulus section 206 to secure the unrolled valve into position in the valve annulus and aortic root. Further, the outflow section 202 may be annealed so as to flare outward and contact the ascending aorta for further anchoring.

With reference to FIGS. 10A-10D and 13-14, an exemplary two-piece heart valve stent comprises a generally ring-shaped primary stent 280 and a tubular secondary stent 350 coupled therewithin. FIGS. 11 and 12 illustrate an alternative secondary stent 300 that could also be coupled with the primary stent 280. The primary stent 280 includes a first side edge 282a that overlaps a second side edge 282b, and a pair of circumferentially disposed end edges 284a, 284b that extend between the side edges. As seen best in FIGS. 10B and 10C, three alignment tabs 286 project radially outward from the second side edge 282b into alignment slots 288. It should be noted that the middle alignment slot 288 is circumferentially staggered with respect to the two alignment slots near the end edges 284a, 284b such that at least one alignment tab 286 resides in one of the slots at all times. Additionally, two pairs of alignment tabs 290 project radially outward from the end edges 284a, 284b at the second side edge 282b, further insuring against misalignment during the unfurling process.

The alignment tabs 286, 290 and slots 288 provide guides for use during unfurling of the primary stent 280 to maintain concentricity about a central axis. That is, as the primary stent 280 transitions between a first, contracted configuration (i.e., a tight spiral) and a second, expanded configuration, the alignment tabs 286 prevent the stent from unrolling or unfurling unevenly to form a cone. Desirably, in the first, contracted configuration, the primary stent 280 is spirally-wound about an axis such that at least one of its windings surrounds another winding, and preferably there are numerous windings to reduce its radial profile. The second side edge 282b resides at the center of the tightly rolled contracted configuration such that as the stent 280 unrolls, the tabs 286 are channeled through the slots 288 and the end edges 284a, 284b are constrained within the tabs 290. As was explained above, only the end edge tabs 290 may be required to insure concentricity during expansion of the valve.

A pair of locking tabs 292 projects inward from the primary stent 280 near the first side edge 282a and engages a cooperating pair of locking notches 294 formed in the second side edge 282b. As can be appreciated from FIG. 10B, the locking tabs 292 and notches 294 prevent the primary stent 280 from contracting once it has been fully expanded. Desirably, a bi-directional locking arrangement is provided to prevent contraction of the stent but also further expansion. There are preferably two locking tabs/slots along the mating edges, desirably located symmetrically about an axial midplane of the stent. Finally, FIG. 10D is a detail of an inwardly directed coupling tab 296 that may be used to couple a secondary stent to the primary stent 280. In the illustrated embodiment, there are three such coupling tabs 296 distributed evenly about the stent.

FIG. 11 illustrates a secondary stent 300 of the present invention in plan view, before being rolled into its contracted configuration. The stent 300 has a generally rectangular periphery defined by a first side edge 302a, a second side edge 302b, and a pair of linear end edges 304a, 304b. Again, the secondary stent 300 comprises a generally sheet-like body that can be rolled into a relatively tight configuration and unrolled into a tube. Three sinus apertures 306a, 306b, 306c are formed in the secondary stent 300, each having a curvilinear cusp 308 and a pair of generally linear commissures 310 on either side of the cusp. An outflow band 312 joins the commissures 310. A pair of combined alignment and locking tabs 316 is sized to translate within respective alignment slots 318 to insure even and concentric unfurling of the stent 300. A pair of locking notches 320 is formed at the end of the alignment slots 318 closest to the first side edge 302a. The locking tabs 316 have an enlarged head joined by a neck to the body of the stent 300 and the locking notches 320 also include a tapered neck 322 that permits passage of the tab neck in only one direction so as to lock it therein.

FIG. 12 is a detailed isolation of overlapping side edges of a secondary stent showing alignment tabs 330 disposed on side edges of the inner layer of the stent. These alignment tabs 330 therefore can replace the alignment tabs 316 and slots 318 of the secondary stent 300 of FIG. 11, although alternative locking structure must be provided.

Figure 14:
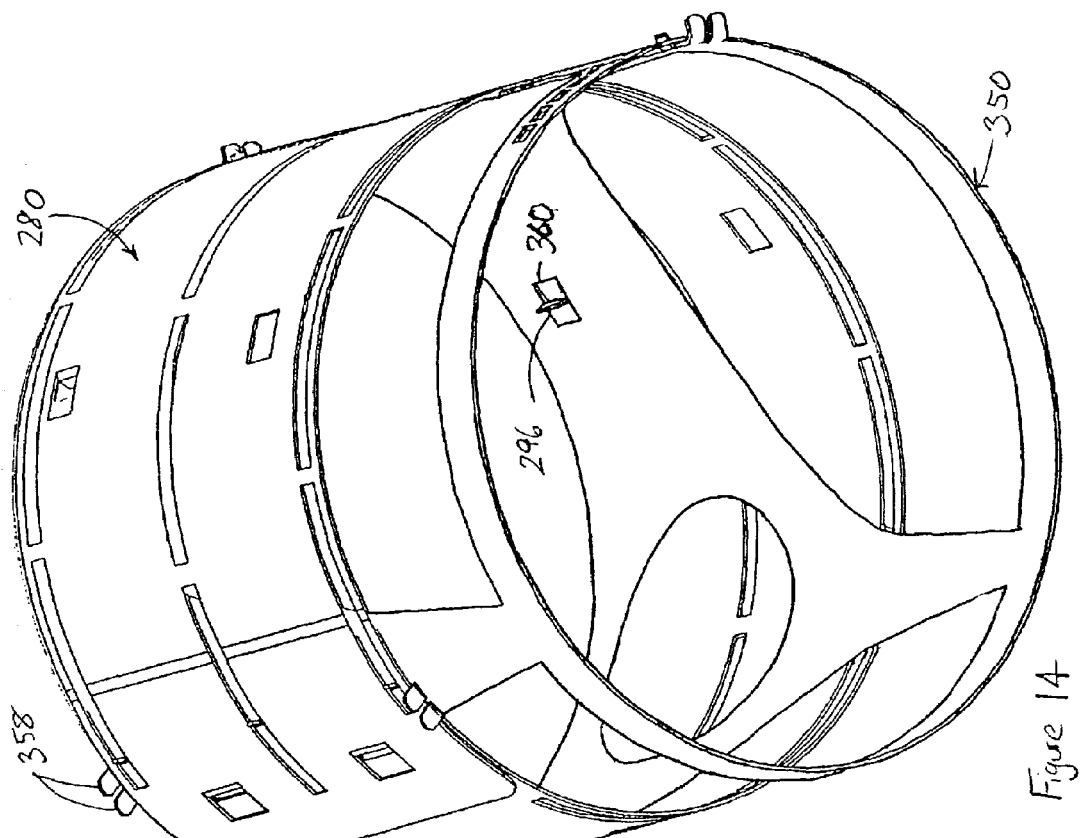
FIG. 14 is a perspective view of a primary stent like that shown in FIG. 10A coupled to a secondary stent like that shown in FIG. 13.
Figure 13:
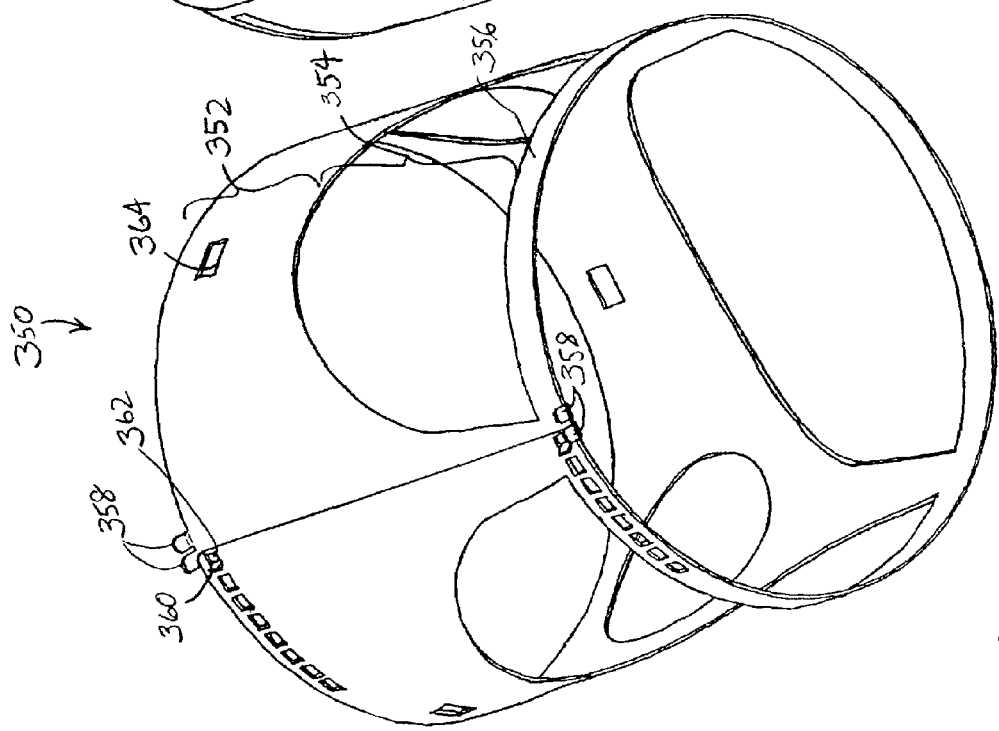
FIG. 13 is a perspective view of an exemplary expanded secondary stent of the present invention similar to that shown in FIG. 11.

FIG. 13 illustrates another exemplary secondary stent 350 of the present invention, and FIG. 14 illustrates the same stent coupled with the primary stent 280 of FIG. 10A. The secondary stent 350 includes many of the same features described above, including a generally solid inflow section 352, a sinus section 354, and an outflow band 356 (again, the leaflet-forming membranes are not shown to better illustrate the stent). The body of the stent 350 includes two pairs of side alignment tabs 358 that prevent the stent 350 from unfurling into a conical form. One or more lockout tabs (not shown) extend outward from one side edge of the stent 350 and engage one or more apertures (not shown) in the other side edge to secure the edges in an overlapping relationship as shown. A plurality of coupling windows 360 is located at evenly-spaced circumferential intervals around the body of the stent 350 to receive and retain coupling tabs 296 extending inward from the primary stent 280 (see FIG. 10D). Note in FIG. 14 that the alignment tabs 358 closely conform to the inflow end of the primary stent 280 and further help retain the stent assembly together. Also, these alignment tabs 358 may serve as anchoring barbs to retain the valve in the host annulus.

In use, the primary stent 280 is first delivered and then unfurled and secured in the native annulus, after which the secondary stent 350 is delivered and then unfurled and locked within the primary stent. The outwardly projecting alignment tabs 290 in the primary stent 280 may double as anchoring barbs to engage the native tissue and help prevent migration of the valve.

The heart valves of the present invention may be implanted using several minimally-invasive approaches, and in one or more stages. For example, the single stent valves described herein may be delivered using a pusher, or along with a balloon catheter, through a large bore cannula or catheter (i.e., tube). The two piece valves may be delivered through a single tube, or through two different tubes in sequence. In one embodiment, the stent having the flexible membranes thereon, may be stored in an unfurled configuration to reduce stress on and damage to the membranes, and then rolled into a compact tube just prior to use. One or two balloons may be used, or the stents can be primarily self-expanding with a balloon or other expansion device used to provide a final deployment force, such as for anchoring barbs in the annulus or locking the rolled stents in the open configuration.

One exemplary implantation procedure begins with selecting and procuring a minimally invasive valve based on size and delivering it to the operating room. Desirably, the valves are stored in their expanded or unrolled configuration in a suitable shipping container. Typically, the flexible membranes or leaflets require hydration and/or a sterile environment, and are stored in a solution. The operating room technician removes the unrolled valve from the shipping container and converts it into a rolled or contracted configuration. This operation can be done manually, or with the assistance of a special apparatus that carefully rolls the valve stent so as to avoid damaging the flexible membranes. For example, one system and method for rolling the valve into its contracted shape while still in the shipping container is disclosed in U.S. application Ser. No. 09/945,392, and another is disclosed in U.S. application Ser. No. 09/815,521. Once rolled into a tight spiral, the valve desirably has a diameter of less than about 20 mm. An aspect ratio of the stents of the present invention is defined as the axial length over the final, expanded diameter. Some of the stents as described above may have a relatively small aspect ratio, desirably less than about 2. The valve is restrained from unrolling by coupling it with a delivery apparatus, and/or by securing it with sutures or other restraining means such as a tubular sleeve.

Once the rolled valve is formed, it is loaded within a delivery tube or catheter and urged down the tube to the implantation site. A pusher or other such device may be used to advance the rolled valve. Once at the site, the tube may be retracted and the rolled valve caused to unfurl on its own. Typically, the valve may be delivered over an inflation balloon to enable plastic deformation/expansion, or the stent may be expanded with a subsequently introduced balloon or mechanical expander.

Figure 15D:
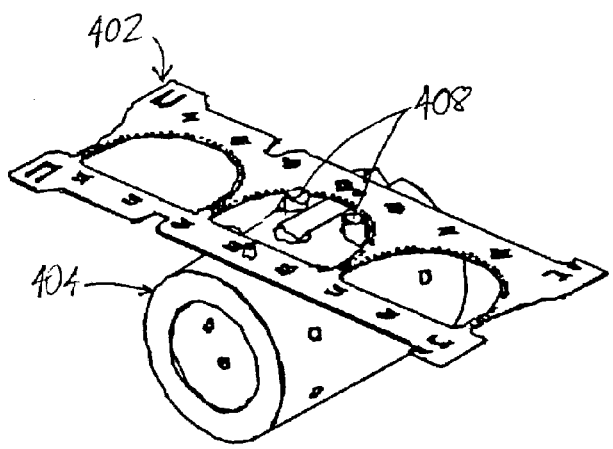

With reference now to FIGS. 15A-15H, an exemplary mandrel 400 for setting the shape of the heart valve stents of the present invention is illustrated in various stages of operation. FIG. 15A shows the mandrel 400 assembled around a heart valve stent 402. The mandrel 400 comprises a tubular inner core 404 around which the stent 402 is compressed by an outer shell 406. The inner core 404 is seen in FIG. 15B, while the outer shell 406 is seen best in FIG. 15C.

The tubular inner core 404 includes a plurality of fixed locating pins 408 extending outward in one direction for mating with the outer shell 406. A plurality of sliding pins 410 project through generally radially oriented apertures 412 through the inner core 404. A pair of end caps 414a, 414b extend into opposite ends of a bore 416 of the inner core 404. The end caps 414a, 414b have elongated threaded sleeves that mate within the bore 416 and pull the end caps together. Each end cap 414a, 414b includes a tapered body 418a, 418b that projects into the bore 416 and acts on the inner ends of the sliding pins 410. Advancement of the tapered bodies 418a, 418b into the bore 416 thus cams the pins 410 outward.

Figure 15E:
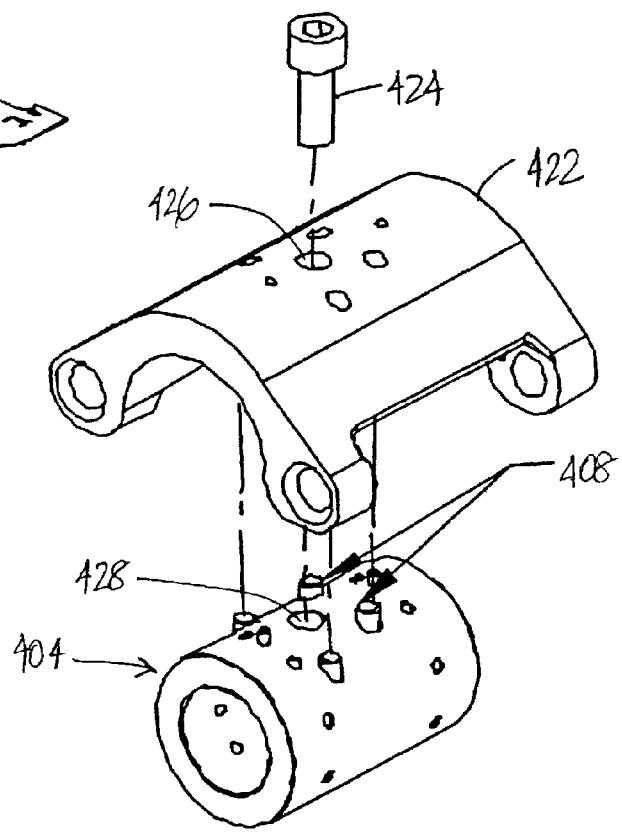
Figure 15F:
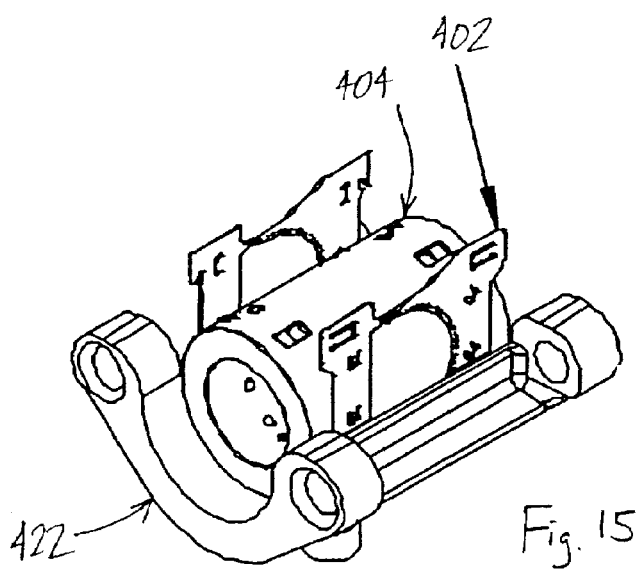

FIGS. 15D-15F illustrate a procedure for securing the valve stent 402 between components of the shape set mandrel. Specifically, FIG. 15D shows the stent 402 positioned over the side of the inner core 404 that has the locating pins 408. There are preferably four such pins 408 that pass through the central sinus aperture of the stent 402. At least two other fixed locating pins 420 (see FIG. 15B) extending outward from the inner core 404 mate with tooling holes (see, e.g., holes 183 in FIG. 5A) in the stent 402. FIG. 15E illustrates how a base portion 422 mates with and fixes to the inner core 404. Specifically, the four locating pins 408 extend into mating apertures in the inner surface of the base portion 422. A bolt 424 passes through a radial aperture 426 in the base portion 422 and into a threaded bore 428 in the inner core 404 to secure the two elements together. Although not shown, this operation is done with the valve stent 402 in place as seen in FIG. 15D. Finally, FIG. 15F shows the inner core 404 assembled with the base portion 422 and stent 402 sandwiched therebetween.

With reference again to FIG. 15C, and also FIG. 15G, the mandrel 406 comprises the base portion 422 and a pair of side portions 430a, 430b pivotally connected thereto. The side portions 430a, 430b are shown pivoted closed over the stent 402 and inner core 404 in FIG. 15A. A pivoting bolt 432 attached to one of the side portions 430a holds the assembly tightly together. The inner surfaces of the base portion 422 and the side portions 430a, 430b are concave and generally cylindrical to closely match the outer surface of the inner core 404. When the mandrel 406 is assembled, the stent 402 is compressed from the inside and the outside. FIG. 15G also illustrates a number of recesses 434, cavities 436, and forming features 438 on the inner surfaces of the side portions 430a, 430b. Similar features are provided on the inner surface of the base portion 422. As will be described, these elements cooperate with the inner core 404 and sliding pins 410 (FIG. 15B) to create a number of different features on the stent 402.

For example, FIG. 15H illustrates the interaction between the sliding pins 410, inner core 404, tapered body 418b, and outer shell 406. Specifically, as the tapered body 418b advances to the left as indicated by arrow 440, the sliding pin 410 displaces upward as indicated by arrow 442 through the aperture 412 and into the recess 434. Although not shown, the stent 402 is held tightly between the core 404 and shell 406. The pins 410 therefore pushes a portion of the stent 402 radially outward. Those of skill the art will understand that variously shaped pins 410 and recesses 434 can be used to form or stamp a variety of features into the stent 402. For example, the curved anchoring elements 170 seen in FIGS. 5B and 5F can be thus formed.

Figure 16:
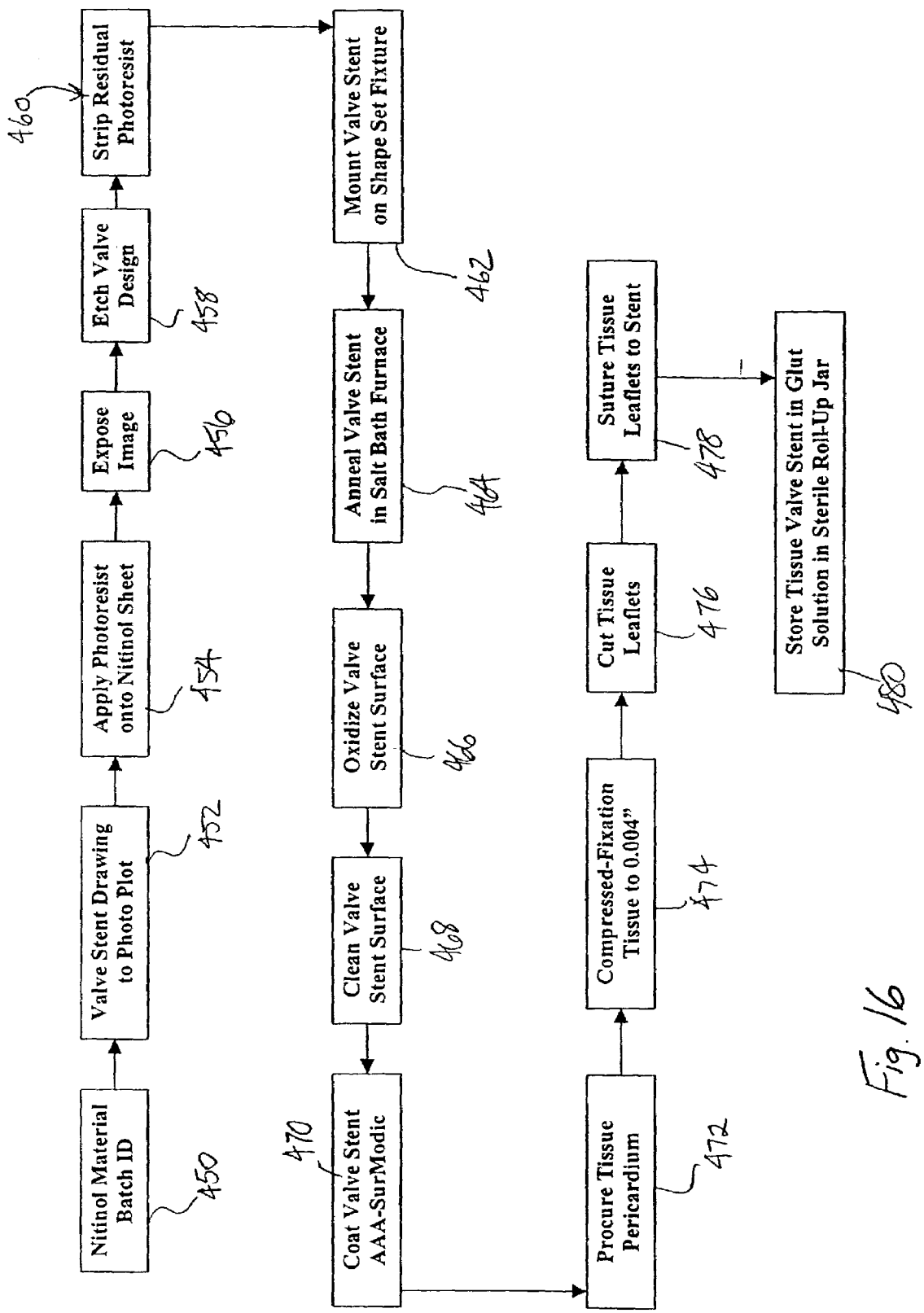
FIG. 16 is a manufacturing flowchart illustrating steps in forming heart valve stents of the present invention.

FIG. 16 is a flowchart of an exemplary manufacturing process for the valve stents of present invention. First of all, flat sheet material is procured, such as Nitinol sheet, as indicated at 450. The outlines of the valve stent are provided to a device that applies a photo resist material onto the Nitinol sheet blank, as indicated in steps 452 and 454. Subsequently, an image on the Nitinol sheet is exposed in step 456, and various features are etched in step 458. The etching process completely removes material in areas where there are cavities or holes in the stent. At locations where the material is only thinned, the etching process is done for a shorter amount of time. Those of skill in the art of chemical etching will understand the parameters to control to result in the stents as described herein. The photo resist material remaining on the Nitinol sheet is then stripped in step 460.

Step 462 involves mounting the flat stent blank into the mandrel 406, as was described above with respect to FIGS. 15A-15H. After securing the valve stent tightly within the mandrel, the entire assembly is placed within a salt bath furnace to anneal the valve stent material into its desired shape. The salt bath may be potassium nitrate. With reference to the valve stent embodiment in FIGS. 4 and 5, the annealing process fixes the relaxed shape of the stent 120 into the circular shape shown in FIGS. 4A-4F, where the side edges are almost but not quite brought together. Again, this results in an outward bias to the valve stent during the expansion process and when the side edges are coupled. Moreover, the circular shape set reduces stresses associated with the natural material elasticity tending to open the stent. That is, if a flat sheet were used and bent into a tube, it would tend to open in a teardrop shape, with high stress at the apex of the teardrop, where the two free edges come together.

Steps 466, 468, and 470 all involve treating the outer surface of the valve stent to be compatible with the subsequently attached flexible membranes, and with the human body. Specifically, step 466 involves oxidizing the stent surface. In step 468 the stent surface is cleaned, such as by mechanical polishing. Finally, the valve stent is coated with a lubricious, biocompatible material, such as Teflon or a polymeric material sold under the name AAA-SurModic.

At this stage in the process, the valve stent is completely formed and ready for assembly with the other components. Step 472 comprises procuring an appropriate biocompatible sheet material for use as the flexible membranes. In one embodiment, the material is pericardium, such as bovine pericardium. If animal tissue such as bovine pericardium is used it may be compressed to reduce its thickness, as shown in step 474. The process for compressing biological tissue for such use is disclosed in co-pending U.S. application Ser. No. 10/141,145, filed May 8, 2002, which disclosure is expressly incorporated by reference herein. For example, the bovine pericardium tissue may be compressed to about 50% of its original thickness. In one specific example, the tissue is compressed to a thickness of about 0.1 mm (0.004 inches). After compression, the leaflet shapes are cut from the bulk material as seen in step 476. The final assembly step of the valve comprises attaching the leaflets to the stent, such as with sutures as in step 478. After assembly, the valve is typically stored in a preservative solution such as glutaraldehyde, as seen in step 480. This is the final manufacturing step, and the valve is not removed from the container until the operating room when it is about to be implanted.

While the foregoing describes the preferred embodiments of the invention, various alternatives, modifications, and equivalents may be used. Moreover, it will be obvious that certain other modifications may be practiced within the scope of the appended claims.

What is claimed is:

1. A method of prosthetic heart valve implantation at an aortic annulus, comprising:
    delivering a rolled prosthetic heart valve to an aortic annulus, the prosthetic heart valve including a stent body having a spirally-wound contracted, first configuration with a first diameter configured for advancement to the aortic annulus and an unwound expanded, second configuration with a maximum second diameter, the prosthetic heart valve further including three flexible membranes attached to the stent body that form heart valve leaflets in the expanded configuration and portions of the stent body between the leaflets defining axially extending commissures;
    unfurling the prosthetic heart valve from the spirally-wound contracted, first configuration to the unwound expanded, second configuration at the aortic annulus; and
    positioning the prosthetic heart valve such that the stent body commissures align with native commissures of the aortic annulus.

2. The method of claim 1, further including anchoring the prosthetic heart valve in its expanded configuration to the aortic annulus.

3. The method of claim 1, wherein native heart valve leaflets of the aortic annulus are left in place and the step of unfurling causes the prosthetic heart valve to contact and outwardly compress native leaflets.

4. The method of claim 1, wherein the step of unfurling further includes ensuring that the prosthetic heart valve remains generally tubular throughout the step of unfurling.

5. The method of claim 1, further including at least one guide on the stent body to ensure the stent body remains generally tubular throughout the step of unfurling.

6. The method of claim 1, wherein the stent body has an annulus section on an inflow end, a sinus section, and an outflow section, the sinus section being between the annulus section and outflow section and having a plurality of sinus apertures.

7. The method of claim 6, wherein the flexible membranes each include an arcuate cusp edge and a free edge, the arcuate cusp edges of the leaflets being attached around one of the sinus apertures.

8. The method of claim 1, wherein the flexible membranes are formed of bioprosthetic tissue.

9. A method of prosthetic heart valve implantation, comprising:
    positioning a rolled prosthetic heart valve at a heart valve annulus, the prosthetic heart valve including a stent body having a spirally-wound contracted, first configuration with a first diameter configured for advancement to the heart valve annulus and an unwound expanded, second configuration with a maximum second diameter, the prosthetic heart valve further including a plurality of flexible, bioprosthetic tissue membranes attached to the stent body that form heart valve leaflets in the expanded configuration, wherein there are three flexible, bioprosthetic tissue membranes that form three heart valve leaflets in the expanded configuration of the stent body, and the stent body further defines axially extending commissures between the three leaflets; and
    unfurling the prosthetic heart valve from the spirally-wound contracted, first configuration to the unwound expanded, second configuration at the heart valve annulus.

10. The method of claim 9, further including anchoring the prosthetic heart valve in its expanded configuration to the heart valve annulus.

11. The method of claim 9, wherein native heart valve leaflets of the heart valve annulus are left in place and the step of unfurling causes the prosthetic heart valve to contact and outwardly compress native leaflets.

12. The method of claim 9, wherein the step of unfurling further includes ensuring that the prosthetic heart valve remains generally tubular.

13. The method of claim 9, further including the step of locking the prosthetic heart valve in its expanded configuration.

14. The method of claim 9, wherein the stent body has an annulus section on an inflow end, a sinus section, and an outflow section, the sinus section being between the annulus section and outflow section and having a plurality of sinus apertures.

15. The method of claim 9, wherein the prosthetic heart valve is configured to be disposed on a distal end portion of a catheter for positioning the prosthetic heart valve at the heart valve annulus.

16. The method of claim 9, further including at least one anchoring element extending radially outward from the stent body for preventing axial migration of the prosthetic heart valve after implantation.

17. The method of claim 9, wherein the flexible membranes each include an arcuate cusp edge and a free edge, and each arcuate cusp edge attaches to the stent body such that the leaflets billow inward upon blood flow in one direction to coapt along an axis of the valve and form fluid occluding surfaces.

18. A method of prosthetic heart valve implantation, comprising:
    providing a rolled prosthetic heart valve having a sheet-like stent body with lockout tabs and slots, the stent body having a spirally-wound contracted, first configuration with a first diameter for delivery to a heart valve annulus and an unwound expanded, second configuration wherein the tabs engage the slots to prevent contraction as well as further expansion, wherein the stent body has an annulus section on an inflow end, a sinus section, and an outflow section, the sinus section being between the annulus section and outflow section, and having a plurality of sinus apertures, and wherein the prosthetic heart valve comprises a plurality of flexible biocompatible membranes incorporated into the stent body that form heart valve leaflets in the expanded configuration, and wherein the flexible membranes each include an arcuate cusp edge and a free edge the arcuate cusp edges of the leaflets being attached around one of the sinus apertures;

positioning the rolled prosthetic heart valve at a heart valve annulus; and unfurling the prosthetic heart valve in a controlled manner from the spirally-wound contracted, first configuration to the unwound expanded, second configuration within the heart valve annulus to ensure that the prosthetic heart valve retains a tubular shape rather than a frustoconical shape throughout the step of unfurling.

19. The method of claim 18, further including anchoring the prosthetic heart valve in its expanded configuration to the heart valve annulus.

20. The method of claim 18, wherein native heart valve leaflets of the heart valve annulus are left in place and the step of unfurling causes the prosthetic heart valve to contact and outwardly compress the native leaflets.

21. The method of claim 18, wherein the step of unfurling further includes ensuring that the prosthetic heart valve remains generally tubular.

22. The method of claim 18, further including the step of locking the prosthetic heart valve in its expanded configuration.

23. The method of claim 18, further including at least one guide to ensure the stent body retains its tubular shape throughout the step of unfurling.

24. The method of claim 23, wherein the stent body defines a pair of opposed side edges that generally mate in the expanded, second configuration, and a pair of opposed end edges that extend between the side edges, and the at least one guide comprises a guide tab extending generally radially along each one of the end edges.

25. The method of claim 18, further including at least one anchoring element extending radially outward from the stent body for preventing axial migration of the heart valve after implantation in the annulus.

26. The method of claim 18, wherein the flexible membranes are formed of bioprosthetic tissue.

27. A method of prosthetic heart valve implantation, comprising:

positioning a rolled prosthetic heart valve at a heart valve annulus, the prosthetic head valve including a stent body having a spirally-wound contracted, first configuration with a first diameter configured for advancement to the heart valve annulus and an unwound expanded, second configuration with a maximum second diameter, and wherein the stent body defines a pair of opposed side edges that generally mate in the expanded, second configuration, and a pair of opposed end edges that extend between the side edges, and at least one tab extending generally radially along each one of the end edges to ensure the stent body expands evenly along an axis when unfurling from the contracted, first configuration to the expanded, second configuration; and unfurling the prosthetic heart valve from the spirally-wound contracted, first configuration to the unwound expanded, second configuration at the heart valve annulus.

28. A method of prosthetic heart valve implantation, comprising:

providing a rolled prosthetic heart valve having a sheet-like stent body with lockout tabs and slots, the stent body having a spirally-wound contracted, first configuration with a first diameter for delivery to a heart valve annulus and an unwound expanded, second configuration wherein the tabs engage the slots to prevent contraction as well as further expansion, wherein the stent body defines a pair of opposed side edges that generally mate in the expanded, second configuration, and a pair of opposed end edges that extend between the side edges, and at least one guide tab extending generally radially along each one of the end edges to ensure the stent body expands evenly along an axis when unfurling from the contracted, first configuration to the expanded, second configuration;

positioning the rolled prosthetic heart valve at a heart valve annulus; and unfurling the prosthetic heart valve from the spirally-wound contracted, first configuration to the unwound expanded, second configuration within the heart valve annulus.

29. A method of prosthetic heart valve implantation, comprising:

positioning a rolled prosthetic heart valve at a heart valve annulus, the prosthetic heart valve including a stent body having a spirally-wound contracted, first configuration with a first diameter configured for advancement to the heart valve annulus and an unwound expanded, second configuration with a maximum second diameter, the prosthetic heart valve further including a plurality of flexible, bioprosthetic tissue membranes attached to the stent body that form heart valve leaflets in the expanded configuration, wherein the stent body defines a pair of opposed side edges that generally mate in the expanded, second configuration, and a pair of opposed end edges that extend between the side edges, and further including at least one tab extending generally radially along each one of the end edges to ensure the stent body expands evenly along an axis when unfurling from the contracted, first configuration to the expanded, second configuration; and unfurling the prosthetic heart valve from the spirally-wound contracted, first configuration to the unwound expanded, second configuration at the heart valve annulus.

30. The method of claim 29, further including the step of locking the prosthetic heart valve in its expanded configuration.

31. The method of claim 29, wherein the stent body has an annulus section on an inflow end, a sinus section, and an outflow section, the sinus section being between the annulus section and outflow section and having a plurality of sinus apertures.

32. The method of claim 29, wherein the flexible membranes each include an arcuate cusp edge and a free edge, and each arcuate cusp edge attaches to the stent body such that the leaflets billow inward upon blood flow in one direction to coapt along an axis of the valve and form fluid occluding surfaces.

33. A method of prosthetic heart valve implantation, comprising:

providing a rolled prosthetic heart valve having a sheet-like stent body with lockout tabs and slots, the stent body having a spirally-wound contracted, first configuration with a first diameter for delivery to a heart valve annulus and an unwound expanded, second configuration wherein the tabs engage the slots to prevent contraction as well as further expansion, wherein the stent body defines a pair of opposed side edges that generally mate in the expanded, second configuration, and a pair of opposed end edges that extend between the side edges, and at least one guide tab extends generally radially along each one of the end edges to ensure the stent body retains its tubular shape throughout the step of unfurling;

positioning the rolled prosthetic heart valve at a heart valve annulus; and unfurling the prosthetic heart valve in a controlled manner from the spirally-wound contracted, first configuration to the unwound expanded, second configuration within the heart valve annulus to ensure that the prosthetic heart valve retains a tubular shape rather than a frustoconical shape throughout the step of unfurling.

* * * * *